US006044490A

United States Patent [19]

Volkert et al.

[11] Patent Number: 6,044,490

[45] **Date of Patent: *Apr. 4, 2000**

[54] PAPER PRODUCT AND METHOD OF MAKING

[75] Inventors: Carolyn K. Volkert, Northfield, Ill.; Andrew M. Volkert, Cardiff By The Sea, Calif.

[73] Assignee: Volkert, Inc., Northfield, Ill.

[ * ] Notice: This patent is subject to a terminal disclaimer.

[21] Appl. No.: 09/277,899

[22] Filed: Mar. 29, 1999

Related U.S. Application Data

[60] Division of application No. 08/763,221, Dec. 10, 1996, Pat. No. 5,887,366, which is a continuation-in-part of application No. 08/286,674, Aug. 5, 1994, Pat. No. 5,588,233.

[51] Int. Cl.[7] .......... A61F 9/00

[52] U.S. Cl. .......... 2/12; 2/200.3; 40/329; 428/43

[58] Field of Search .......... 2/12, 200.3; 40/124.08, 40/539, 329; 428/43; 446/148

[56] References Cited

U.S. PATENT DOCUMENTS

| | | | |
|---|---|---|---|
| 2,152,299 | 3/1939 | Arndt | 40/126 |
| 2,156,815 | 5/1939 | Levy | 40/125 |
| 2,544,783 | 3/1951 | Freedman et al. | 40/126 |
| 2,609,639 | 9/1952 | Barker | 46/34 |
| 2,742,723 | 4/1956 | Klein et al. | 446/148 |
| 3,995,383 | 12/1976 | Penick et al. | 40/126 A |
| 4,103,444 | 8/1978 | Jones et al. | 40/124.1 |
| 4,149,630 | 4/1979 | Transport | 206/45.24 |
| 4,592,573 | 6/1986 | Crowell | 283/56 |
| 4,833,802 | 5/1989 | Volkert | 40/121.1 |
| 5,022,681 | 6/1991 | Penick | 446/148 |
| 5,181,901 | 1/1993 | Volkert | 493/331 |

*Primary Examiner*—Diana Oleksa
*Attorney, Agent, or Firm*—Fitch, Even, Tabin & Flannery

[57] ABSTRACT

Various sheet material blanks comprising one or a plurality of interconnected panels are fabricated so that a stand-out structure die-cut into one panel upon manipulation assumes an attention-attracting, 3-dimensional orientation. The various configurations are such that particular advantages may be obtained through mass production,and machine-assembly methods can profitably be used to construct certain configurations. A variety of methods are shown for efficiently producing such pieces via mass-production, including items having multiple stand-out structures. Flat individual blanks in sheet form are particularly adapted to be conveyed through laser printers, copy machines and other suitable imprinting equipment in order to inexpensively personalize such blanks, which can be used to create a variety of different 3-dimensional items, including novelty sunvisors.

18 Claims, 13 Drawing Sheets

109
93a
99a
93d
103
97a
101
103a
101a
93c 93d
93a
109
99a
97a
103
93b
101
93c 109
93b
107
101a
101
101
93d
108
SEVER
93a
97
97
91
FOLD UPPER HALF
97
93a
101a
101
105
93b
93c
103
103a
95
99
93d
FOLD
APPLY ADHESIVE
FOLD
DIE-CUT
APPLY ADHESIVE

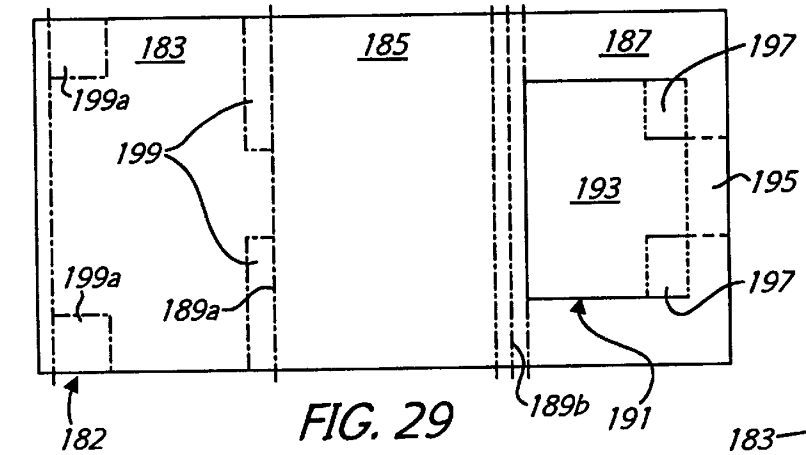
FIG. 29
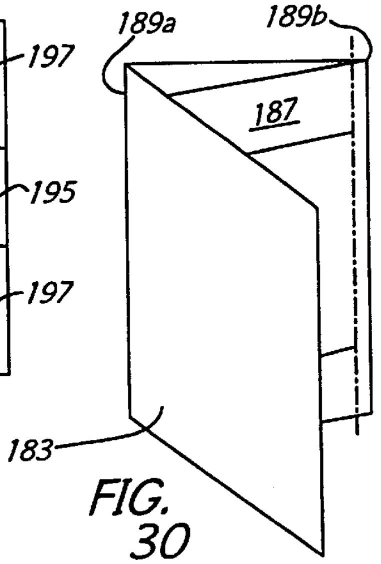
FIG. 30
FIG. 31
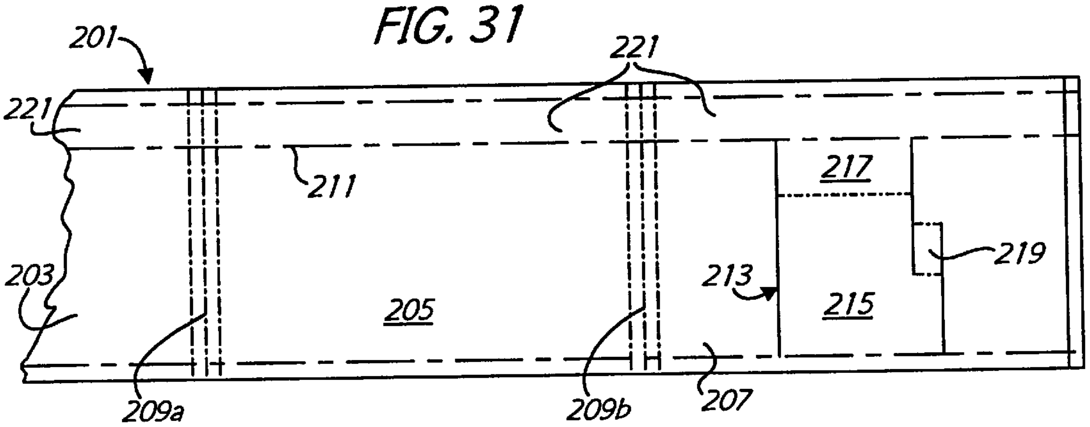
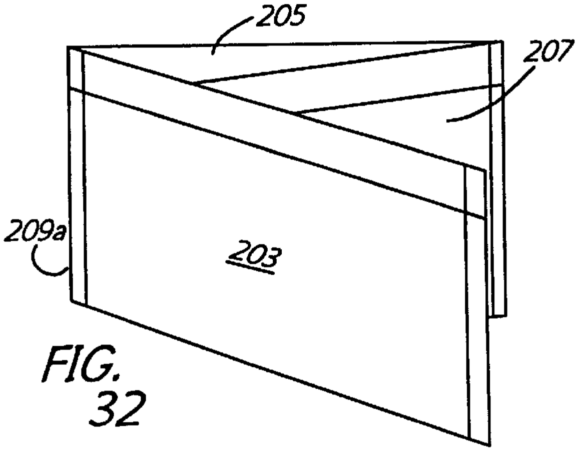
FIG. 32
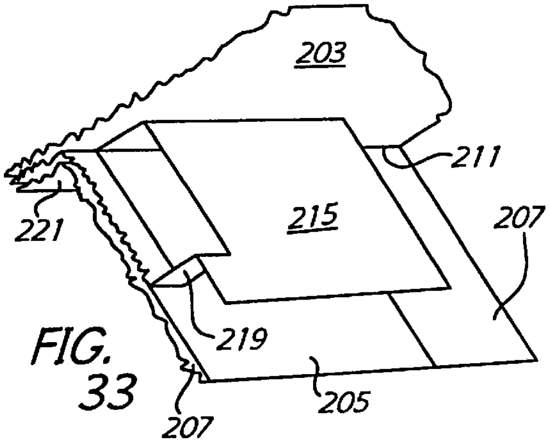
FIG. 33

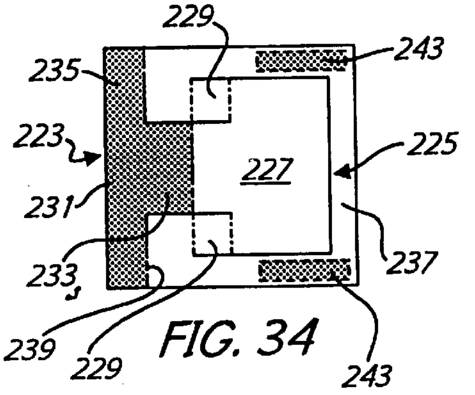
FIG. 34
FIG. 35
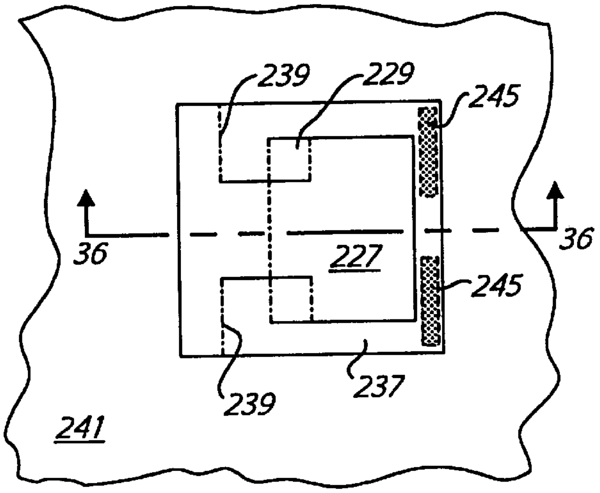
FIG. 36
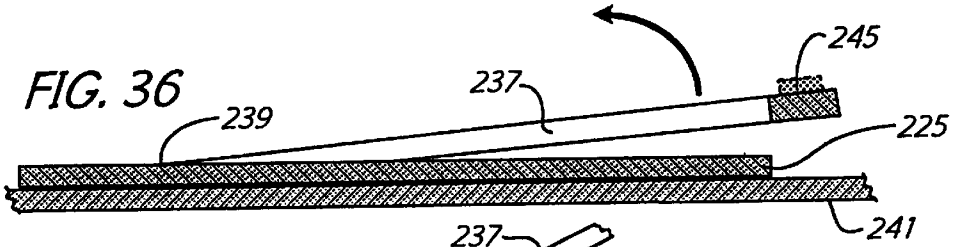
FIG. 37
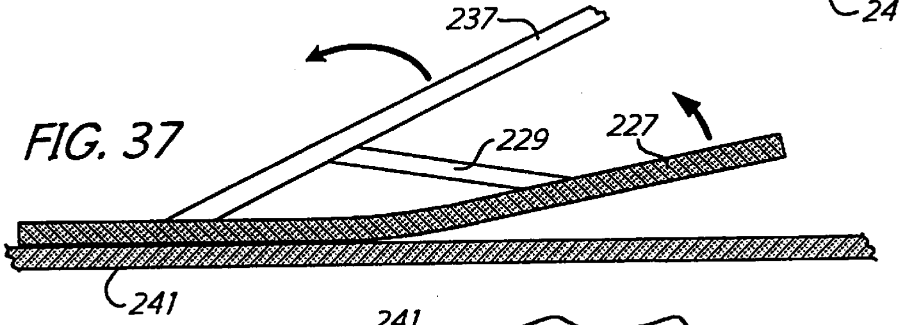
FIG. 38
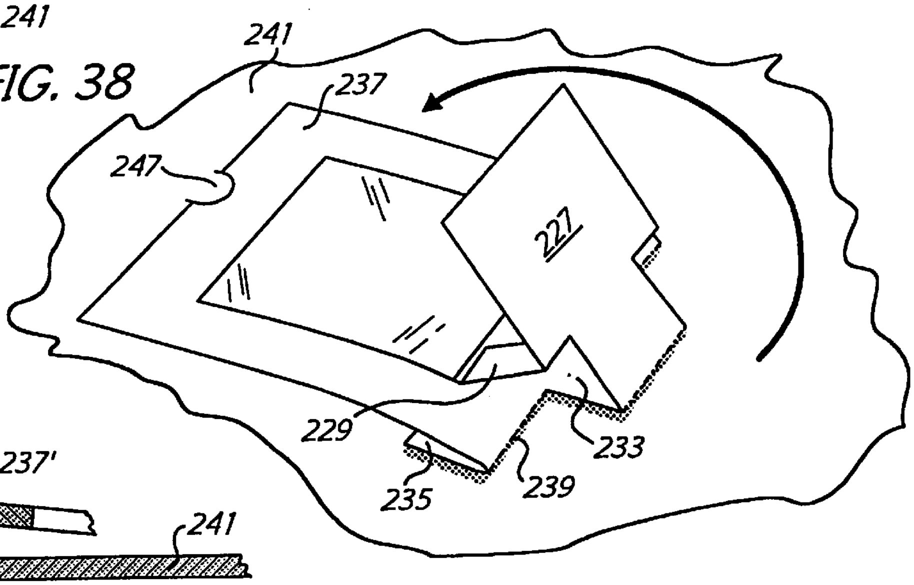
FIG. 38A
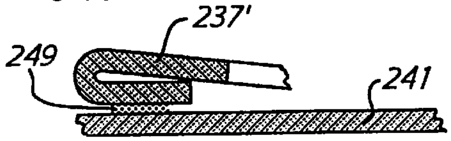

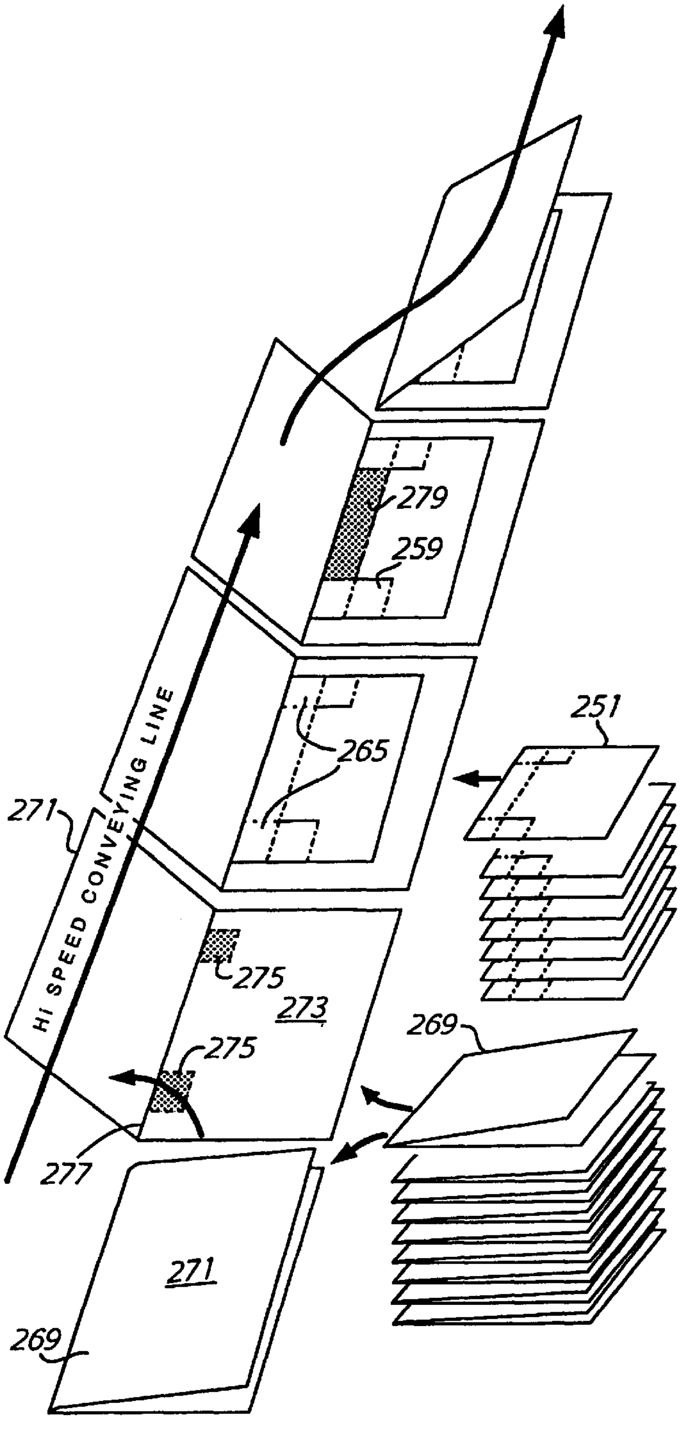
FIG. 40
FIG. 39
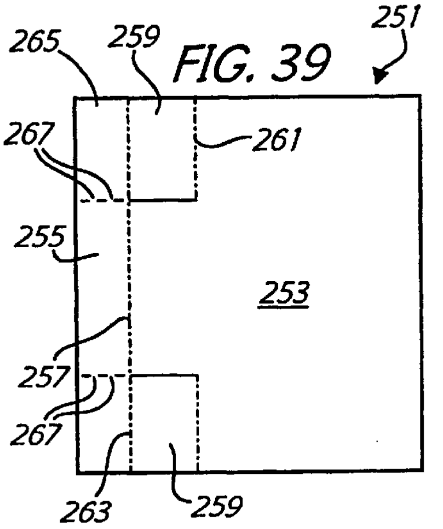
FIG. 41
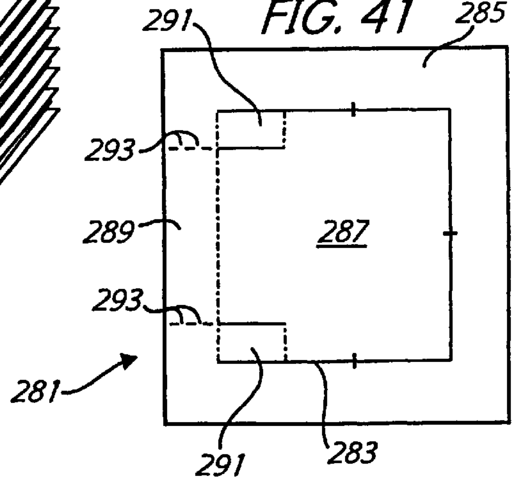

PAPER PRODUCT AND METHOD OF MAKING

This application is a divisional of our application Ser. No. 08/763,221, now U.S. Pat. No. 5,887,366 (Mar. 30, 1999) which is a continuation-in-part of our application Ser. No. 08/286,674, filed Aug. 5, 1994, now U.S. Pat. No. 5,588,233, the disclosures of which are incorporated herein by reference.

This invention relates generally to promotional items made of paper or other sheet material, and more particularly, it relates to promotional sheet material items, particularly those which can be mass-produced, either from a continuous web or from separate sheets, by die-cutting and application of adhesive or other bonding material and which result in an attractive, attention-getting final product.

BACKGROUND OF THE INVENTION

Three-dimensional structural arrangements have long been used in greeting cards and the like and have fairly recently become frequently used in advertising and in other promotional endeavors.

U.S. Pat. Nos. 2,609,639, and 2,152,299 are generally representative of patents which show techniques sometimes referred to as "box-folds" that have been used in greeting cards and the like. U.S. Pat. No. 4,103,444 shows the use of this general technique in making advertising leaflets (see FIG. 5) and the use of strips from one panel to open a flap in an opposite panel. U.S. Pat. No. 4,592,573 shows the use of this technique in stationery items.

Such pieces have now become generally available to the advertising field as a result of the developments shown in several earlier patents, particularly U.S. Pat. No. 3,995,388, issued Dec. 7, 1976, which discloses methods for making pop-up paper products having significant advantages over hand-assembly methods that had been generally theretofore employed. U.S. Pat. No. 4,146,983, issued Apr. 3, 1979, discloses other methods for making novel promotional items, particularly those which are designed to present a plurality of coupons or the like to a recipient upon the opening of a folder. U.S. Pat. Nos. 4,337,589, 4,349,973, 4,833,802, and 4,963,125 disclose still other manufacturing techniques that are specifically suited for mass production of pop-up advertising pieces on a web-press or the like, the disclosures of which patents are incorporated herein by reference.

The foregoing patents describe different manufacturing techniques useful for making advertising and promotional pop-ups as a part of a continuous web arrangement, and pop-ups such as these have been frequently used to create impact and enjoyment in books, in greeting cards and in advertising inserts. These advances in designs and in manufacturing methods have enabled the volume production of such products at significant cost savings and thus have increased their use.

A particularly attractive characteristic of such dimensional items is the construction of a pop-up element which rises upward from a flat, substantially single plane to assume a three-dimensional orientation upon the opening of a pair of cover pieces or basepieces, which may generally form a folder inside of which the pop-up is located. By attaching pop-up elements of these general types to opposite panels of a pair of basepieces, for example along angles created by lines of weakness (e.g. score lines and/or perforations) in combination with adhesive bonds, it is possible to create pressure or stress points on each such bond which, upon opening of one cover, cause the pop-up to be erected. The pressure or stress which is created upon opening is usually sufficient so that, when the cover is manually released, it will draw the cover either partially or entirely closed.

Although substantial design effort has heretofore been expended in creating a variety of different dimensional structures and designs, improved designs continue to be sought, as are methods for mass production of such improved designs.

SUMMARY OF THE INVENTION

It has now been found that an attention-attracting sheet material item can be provided by die-cutting only a single panel from a pair of first and second facing panels which are hinged together along a straight line, e.g. fold-line, in the final item. Such a die-cut in the first panel creates a stand-out structure which should contain at least one line of weakness and which contains a linkage that preferably interconnects the stand-out to the remainder of the first sheet material panel. This one line of weakness preferably extends parallel to the hinge line and creates at least one subpanel hinged to the main body panel of the die-cut stand-out. By applying adhesive or the like onto the sheet material in only a single area, one subpanel can be interconnected to the second facing panel to create an assemblage which, upon the unfolding of the first and second panels, causes the stand-out structure to prominently move out of the plane of the first panel from which it has been die-cut while remaining substantially parallel thereto in an attention-attracting mode. In another embodiment of the invention, the die-cut structure has a main panel which remains directly hinged to the remainder of the first panel and contains a linkage which remains hinged to it that is appropriately adhered to the imperforate facing panel. In such an arrangement, the die-cut structure may be hinged along a line at an angle to the fold-line between the facing panel, or multiple die-cut panels might be provided as a part of a 3 or 4-panel folded item wherein one structure moves through an opening provided in the die-cut adjacent panel. These designs wherein die-cutting occurs in only a single panel lends themselves to considerable savings in material, enhance structural aesthetics and facilitate mass production methods because the region of a continuous web, or even a single sheet, which constitutes an imperforate panel can be readily conveyed under tension and run at high speed, permitting the region wherein the die-cut structure is located to be manipulated, by mechanical folding or the equivalent, into superimposition thereatop. In addition, high-speed mass production methods become particularly feasible when adhesive or other bonding application is effected in a single location on one panel on each item or piece.

BRIEF DESCRIPTION OF THE DRAWINGS

FIG. 29 is a plan view of yet another blank embodying various features of the present invention having three panels which has been die-cut preliminary to forming a dimensional item.

FIG. 30 is a perspective view showing steps in the fabrication of the dimensional items from the blank of FIG. 29.

FIG. 31 is a plan view of still another blank, which also embodies various features of the present invention, having three panels which has been die-cut preliminary to forming a dimensional item having a false backbone.

FIG. 32 is a perspective view of the blank of FIG. 31 showing steps in the fabrication of the dimensional item.

FIG. 33 is a fragmentary perspective viewing showing the fabricated item formed from the blank of FIG. 31 as it would appear when being opened by the recipient.

FIG. 34 is a plan view looking at the underside of a single panel blank embodying various features of the present invention which has been die-cut for the fabrication of a 3-dimensional item.

FIG. 35 is a plan view showing the upper surface of the blank of FIG. 34 disposed upon a supporting surface of greater dimensions.

FIG. 36 is a sectional view, enlarged in size, taken generally along the line 36—36 of FIG. 35 and showing a step in the manipulation of the blank to create a 3-dimensional item.

FIG. 37 is a view similar to FIG. 36 showing further movement of the blank in its manipulation.

FIG. 38 is a perspective view of the blank of FIG. 34 illustrating the final manipulation of the blank to create the 3-dimensional item.

FIG. 38A is a fragmentary sectional view showing the frame portion of a modified version of the blank of FIG. 38 in a similar erected configuration.

FIG. 39 is a plan view of another single panel blank embodying various features of the present invention which has been die-cut preliminary to its insertion into a folder to form a dimensional item.

FIG. 40 is a schematic perspective view showing the fabrication of a 3-dimensional item employing the blank of FIG. 39.

FIG. 41 is a perspective view showing an alternative embodiment of a blank similar to that shown in FIG. 39.

DETAILED DESCRIPTION OF THE PREFERRED EMBODIMENTS

Figure 1A:
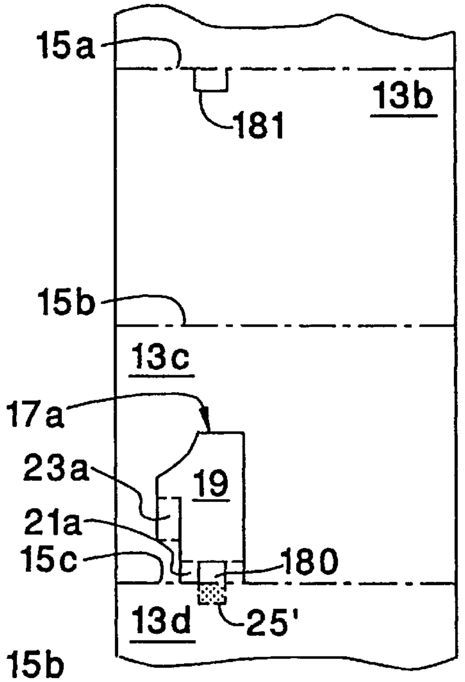
FIG. 1A is a fragmentary plan view of a modified blank similar to that of FIG. 1.
Figure 1:
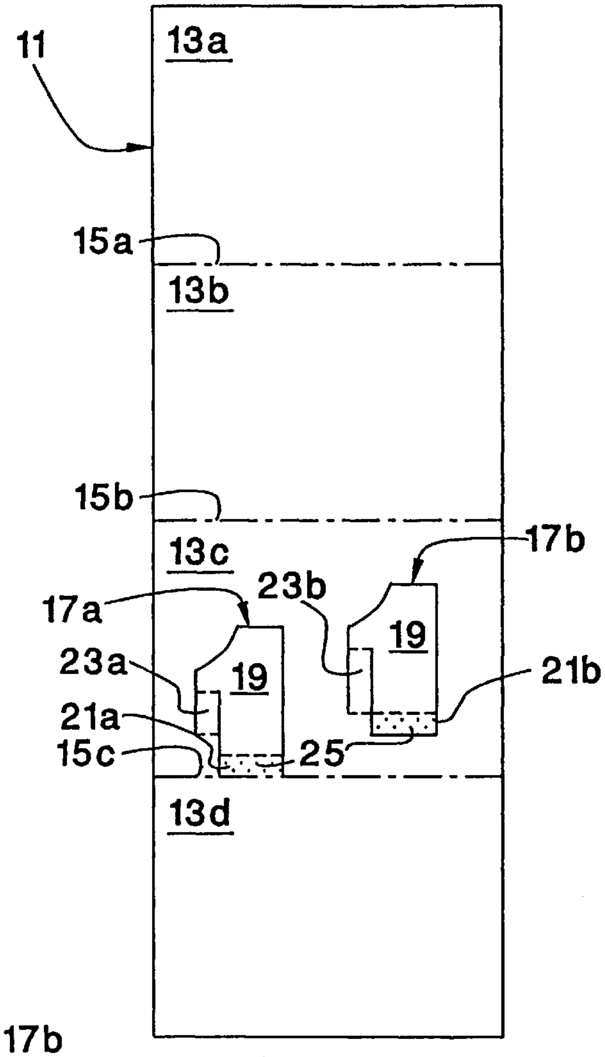
FIG. 1 is a plan view of a blank having four panels which has been die-cut preliminary to forming a dimensional item embodying various features of the present invention.

Illustrated in FIG. 1 is a blank 11 which is designed to be folded to create an attention-attracting dimensional sheet material item. The blank 11 includes 4 panels 13*a, b, c* and *d*, of equal dimension which are interconnected to one another along fold-lines 15*a, b* and *c* which, if desired, can be lines of weakness formed in the sheet material of the blank itself by scoring, creasing, perforating or the like. Any suitable sheet material can be used, such as paper, fiberboard, lightweight plastic or the like; however, a medium weight paper stock, such as that often seen in greeting cards, may be preferred in many instances. Die-cut into panel 13*c* are two structurally similar stand-out structures 17*a* and 17*b* each having generally the shape of the numeral 1. Each stand-out structure has a main body portion 19 in the shape of the numeral 1, an underlying rectangular subpanel 21*a, b* and a link 23*a, b* which is connected or hinged by a line of weakness at its upper end to the main body 19 and at its lower end to the remainder of the overall panel 13*c*. The lower subpanels 21*a* and *b* are also connected or hinged by lines of weakness to the bottom of the respective subpanel 19. At its lower edge, the subpanel 21*a* is hinged to the panel 13*d* along the foldline 15*c*, while the lower edge of subpanel 21*b* is die-cut so as to be free of any connection.

Figure 2:
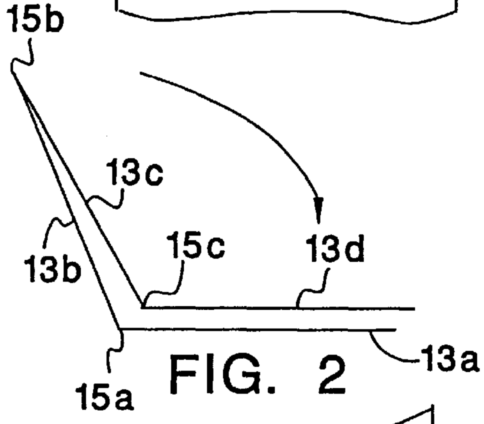
FIG. 2 is a side view of the blank of FIG. 1 showing a step in the fabrication of the dimensional item.

In the illustrated embodiment, an adhesive pattern 25 is applied to the surface of each subpanel 21. Any suitable adhesive, e.g., hot-melt or solvent-based, can be used in such a fabrication process. Such permanent-type adhesive is understood to be such as to have a bond strength that is generally higher than the tear strength of the fibers. Other such adhesive arrangements, including heat, ultrasonic or RF-activated adhesives or micro-encapsulated adhesives, can alternatively be used. If desired, coadhesive patterns of a material that will only adhere to itself can be applied to the appropriate locations of opposite surfaces, as is known in this art. The blank 11 is then first folded along the fold-line 15*b*, and then it is simultaneously folded along fold-lines 15*a* and 15*c* as illustrated in FIG. 2. The subsequent folding step brings panels 13*c* and 13*d* into contact with each other, causing the adhesive 25 to join the surfaces of the subpanels 21*a, b* to mirror-image locations on the facing panel 13*d.*

Figure 3:
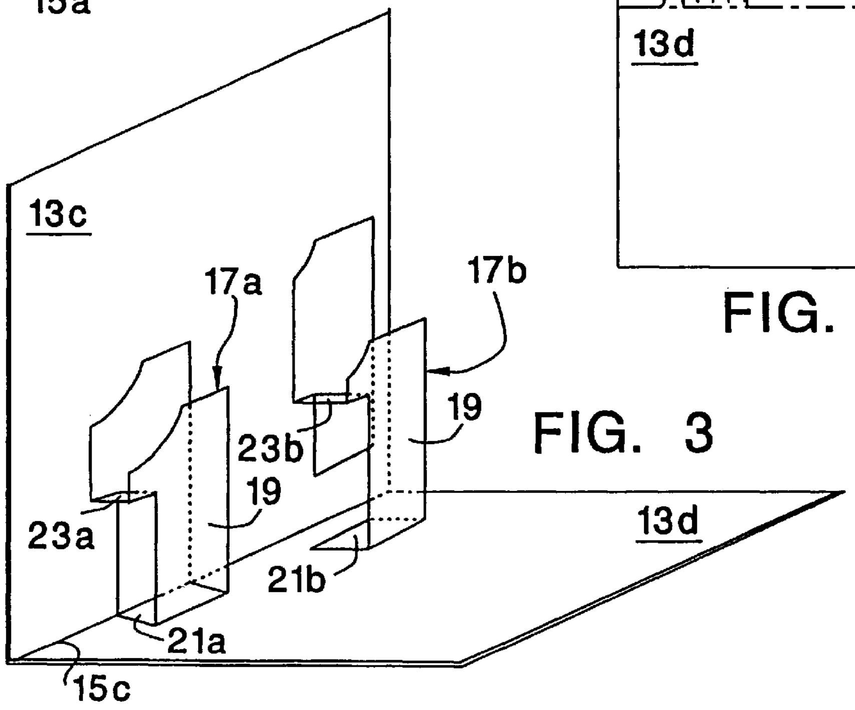
FIG. 3 is a perspective view showing the dimensional item of FIG. 1 in its opened orientation following fabrication.

When the folded dimensional piece is opened as illustrated in FIG. 3, the panel 13*c* moves away from the panel 13*d*, and the subpanels 21, which are affixed by the adhesive pattern 25 to the surface of the imperforate panel 13*d*, move with the panel 13*d* because the lower edge of the subpanel 21*b* is die-cut from the panel 13*c*. This causes the stand-outs 17 to assume a 3-dimensional orientation guided by the links 23*a, b* which interconnect the subpanels 19 and the remainder of the panel 13*c*. The links 23*a* and 23*b* are respectively proportioned to allow the stand-out to assume an orientation generally parallel to the panel 13*c*, in an attractive attention-getting mode.

Figure 4:
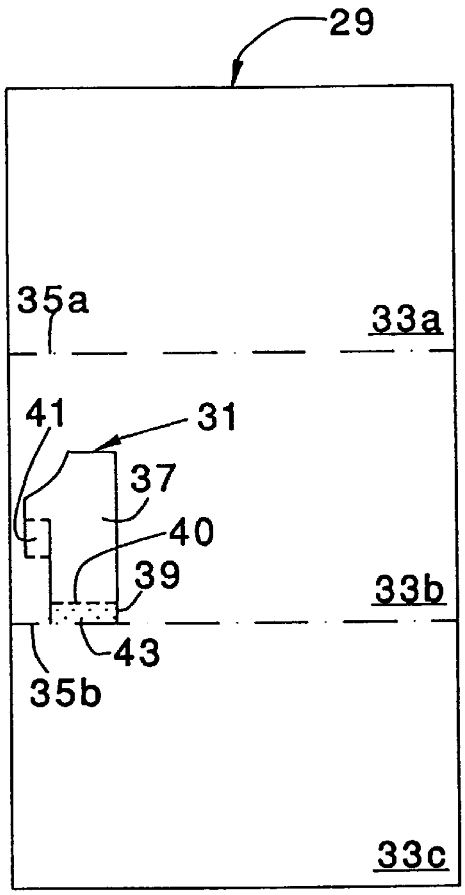
FIG. 4 is a plan view of a sheet of letter-size stationery or the like which has been die-cut and treated to embody various features of the invention.
Figure 5:
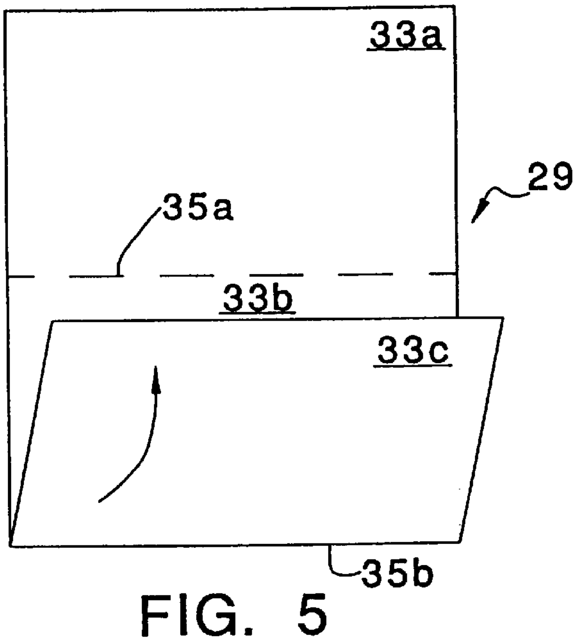
FIG. 5 shows a first step in the folding of the letter stationery of FIG. 4 which can be accomplished automatically or semi-automatically following printing if mass production distribution is intended.
Figure 6:
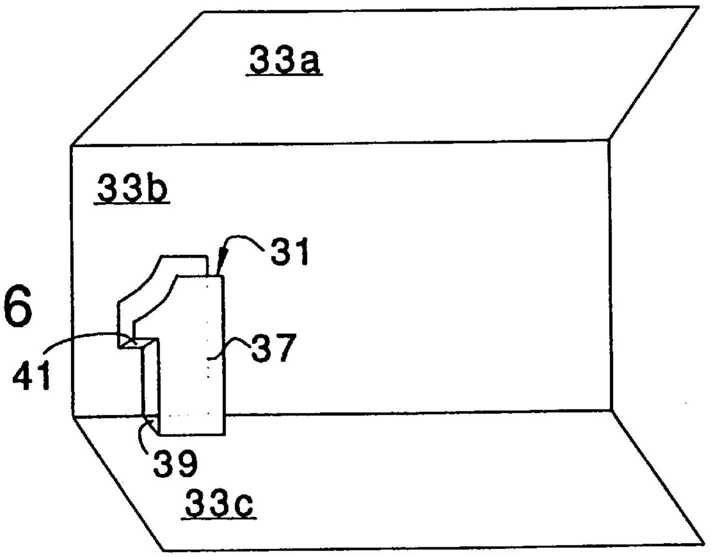
FIG. 6 is a perspective view showing the letter of FIG. 4 as it would appear when opened by the recipient.

Depicted in FIGS. 4, 5 and 6 is a sheet 29, which may be a sheet of letter-writing stationery or the like, into which a stand-out structure 31 has been die-cut. The stand-out structure is located in the central panel of three panels 33*a*, 33*b* and 33*c* of generally equal dimension. These panels can be separated from one another by lines of weakness 35*a* and 35*b*, if desired, or indicia can simply be printed on the sheet 29 along the edges to show where folding should take place. The stand-out structure 31 has a main body portion 37 in the shape of the numeral 1, an underlying rectangular subpanel 39 which is hinged to the main body portion 37 along line of weakness 40 and to the panel 33*c* along the fold-line 35*b*. A link 41 is respectively hinged to the main body 37 and to the remainder of the panel 33*b*. A suitable adhesive pattern 43 is applied to the subpanel 39. If the sheet is to be used as stationery, it may be desirable to apply remoistenable adhesive or to apply pressure-sensitive adhesive covered by a release layer.

After printing or writing on the sheet 29 has been completed, the adhesive 43 is activated, as by moistening the adhesive or by removing a release layer, and the panel 33*c* is folded along the fold-line 35*b* so that it comes into surface-to-surface contact with the panel 33*b*, as depicted in FIG. 5. As a result of this folding step, the subpanel 39 becomes adhered to the surface of the panel 33*c*. Finally, the panel 33*a* is folded along the fold-line 35*a* to complete the folding of the sheet 29, and it is delivered as by mailing to a recipient. Upon opening by the recipient, the stand-out structure 31 becomes prominently and attractively displayed because the subpanel 37 moves away from the plane of the panel 33*b*, guided by the appropriately proportioned linkage arm 41, and assumes an orientation generally parallel thereto in an attention-attracting fashion.

Figure 7:
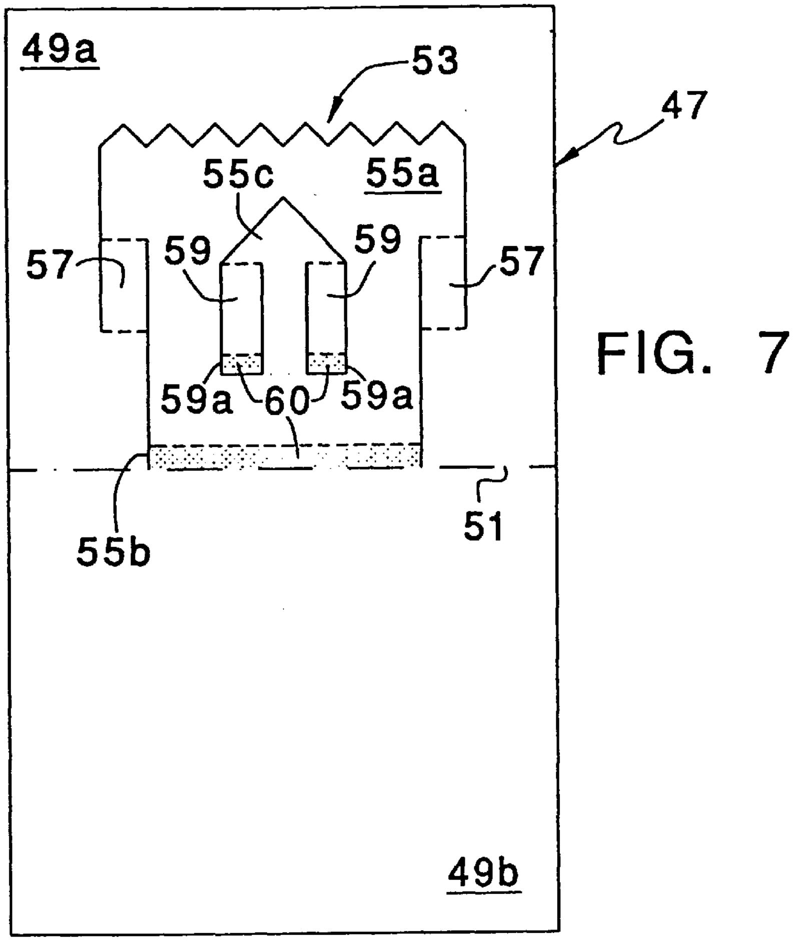
FIG. 7 is a plan view of another blank which has been die-cut and treated so as to provide an intermediate piece ready for fabrication into a dimensional piece similar to that shown in FIGS. 1–3.
Figure 8:
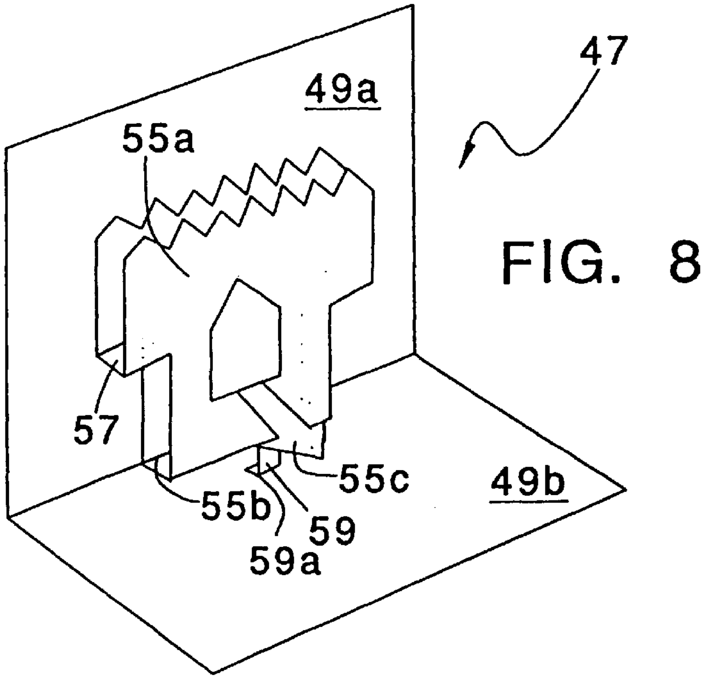
FIG. 8 is a perspective view of the finished piece formed from the blank of FIG. 7 shown in its opened position.

Illustrated in FIGS. 7 and 8 is another blank 47 which is formed to have a pair of panels 49*a* and 49*b* of equal dimension hinged to each other along a line of weakness 51. Die-cut into the upper panel 49*a* is a stand-out structure 53 which includes a main body portion 55*a*, an underlying subpanel 55*b* and a central, arrow-like subpanel 55*c* which is die-cut in the center of the main body 55*a*. The subpanel 55*b* is connected along its lower edge to the panel 49*b* by the fold-line 51; along its upper edge, it is hinged along a line of weakness to the main body 55*a*. A pair of laterally located linkages 57 respectively interconnect flanking regions of the main subpanel 55*a* of the stand-out structure to the remainder of the overall panel 49*a*. A pair of secondary linkages 59 are hinged at their upper ends to the arrow subpanel 55*c*; they include auxiliary subpanel portions 59*a* at their lower ends which are die-cut at the bottom from the remainder of the main body 55*a*, thus remaining connected along an upper line of weakness to the secondary links 59. A pattern of adhesive or other bonding material 60 is applied to the subpanel 55*b* and to the auxiliary subpanels 59*a*. As a result, these three rectangular regions become affixed to the surface of the panel 49*b* when the die-cut blank 47 is folded along the line 51 so as to superimpose one panel 49*a* or *b* atop the other, creating a piece that includes this stand-out structure.

When the completed piece is opened as shown in FIG. 8, the stand-out structure 53 assumes a 3-dimensional configuration, with the panel 55*a* assuming an orientation generally parallel to the plane of the panel 49*a* moved by the affixation of the subpanel 55*b* to the panel 49*b*, and guided by the appropriately proportioned links 57. However, the arrow-like subpanel 55*c* assumes an orientation generally perpendicular to the panel 49*a* as a result of the attachment of the auxiliary subpanels 59*a* at the lower ends of the links secondary 59 to a more central region of the panel 49*b*. To present a clean appearance, a line of weakness is preferably provided at the base of the arrow subpanel 55*c*.

Figure 9:
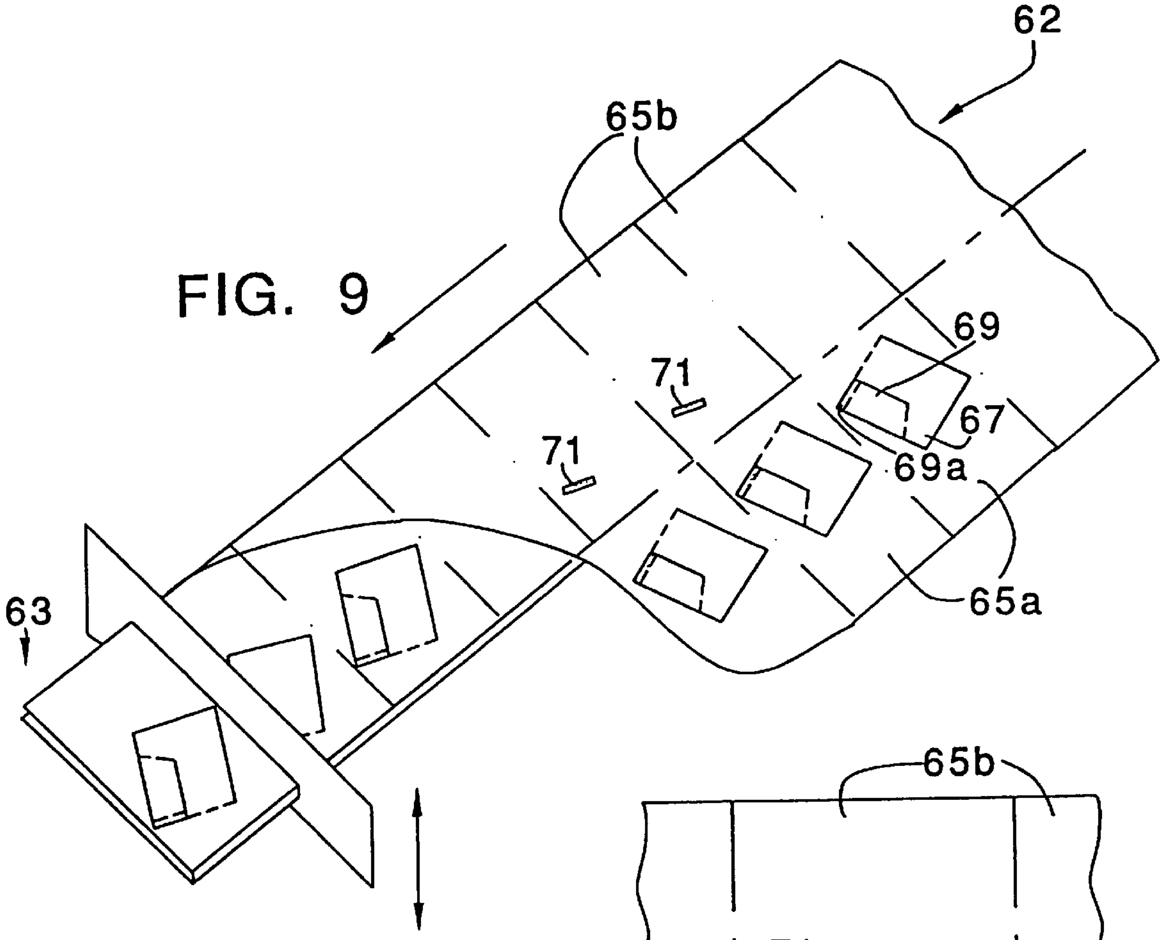
FIG. 9 is a perspective view showing a continuous web which is being die-cut and treated to fabricate a series of structurally identical dimensional pieces embodying various features of the invention.
Figure 10:
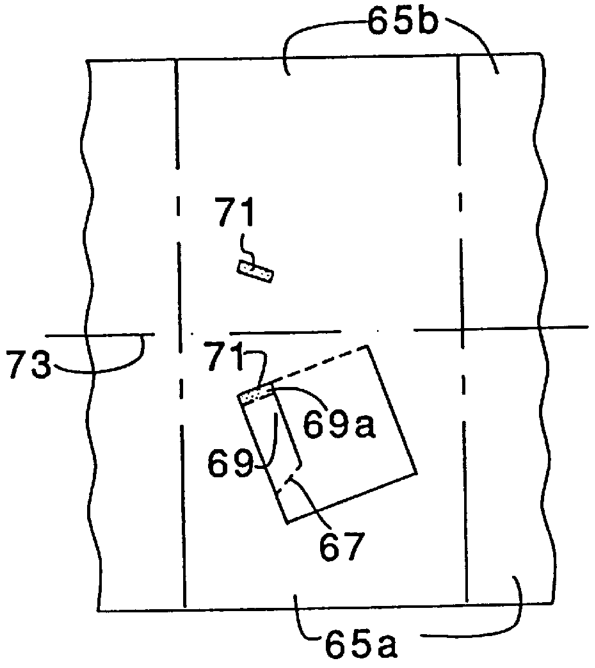
FIG. 10 is a fragmentary plan view of a section of the web being operated upon in the method of FIG. 9.

Illustrated in FIG. 9 is a continuously moving web 62 which may be fed from a roll of sheet material or from a web press or the like, which web is designed to create a plurality of structurally identical, dimensional pieces 63. As best seen in FIG. 10, each of the pieces is designed to be fashioned from a pair of panels 65*a* and 65*b* of generally equal dimension. As the web moves from right to left in FIG. 9, the panels 65*a* are die-cut to form a stand-out structure having a main body 67 located generally centrally within the panel together with a linkage arm 69 hinged to the main body 67. The linkage arm 69 has a subpanel 69*a* at its free end destined for affixation to the opposite panel 65*b*. Following the die-cutting step, coadhesive patterns 71 are applied to both panels 65*a* and 65*b* so that coadhesive 71 covers the subpanel 69*a* as well as a corresponding aligned location on the facing panel 65*b*. Next, the web 62 is folded in half along a line 73 which then becomes a fold-line for the ultimate piece 63. When the panels 65*a* and 65*b* are brought into surface-to-surface contact with each other, the regions carrying the coadhesive become affixed to each other, i.e. the subpanel 69*a* becomes affixed to the panel 65*b*. It should be understood, of course, that instead of applying coadhesive to both panels, adhesive could be applied to one panel or the other to create a similar joinder upon the folding of the web in half. Because the panels 65*b* are imperforate, high tension can be maintained in this half of the web while the die-cut half of the web is folded over it, thus permitting high-speed operation.

Figure 11:
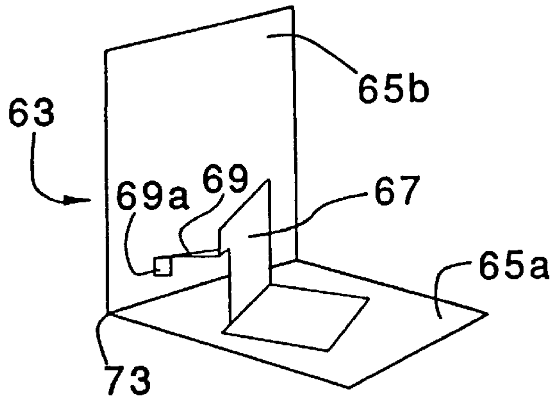
FIG. 11 is a perspective view showing a piece produced from the web of FIG. 10 in its opened orientation.

Following folding, as depicted in FIG. 9, the web is severed by a suitable cutter which may be reciprocating as shown or any other suitable cutter can be employed so as to cut the web into a series of individual, structurally identical pieces 63. Alternatively the pieces 63 could be re-rolled, fan-folded in stacks or severed in multiples, e.g. of 3. When an individual piece 63 is opened, as depicted in FIG. 11, the joinder of the subpanel 69*a* to the panel 65*b* causes the link 69 to pull the stand-out structure from the plane of the panel 65*a* and prominently display it in 3-dimensional configuration. Because the main body 67 is hinged at an angle of about 25° to the fold-line 73, it presents an unusual and attractive appearance.

Illustrated in FIGS. 12 through 16 is an example as to how the invention may be utilized in the growing field of personalized greeting cards or the like which are printed at the point of sale to the customer by a computer-driven laser printer or the like from a roll of sheet material stock.

Figures 12, 13, 14A, 14B, 15A, 15B, 16:
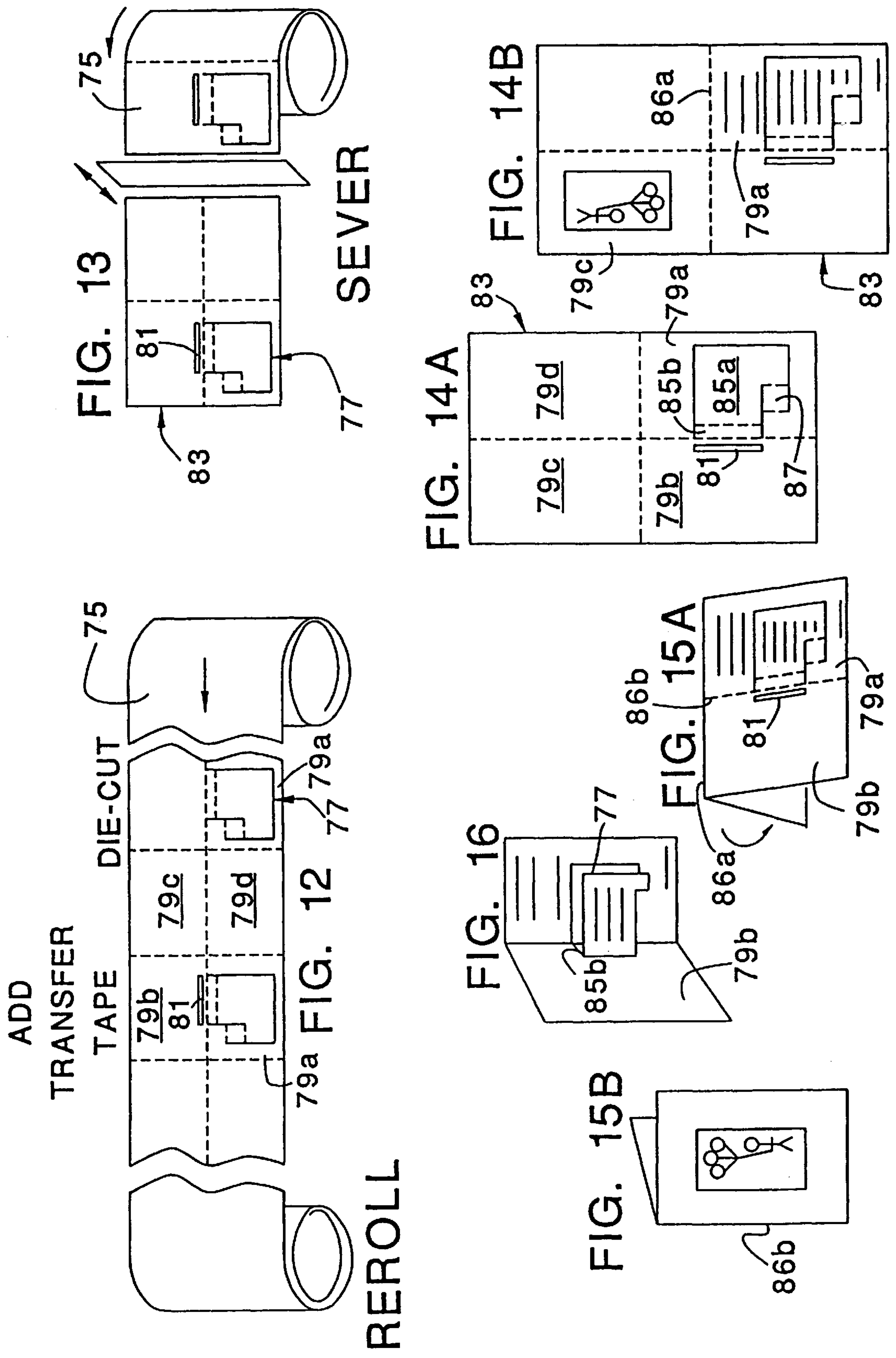
FIG. 12 is a perspective schematic view showing a continuous web of sheet material being die-cut, processed and then re-rolled.
FIG. 13 shows a single item being severed from a roll fabricated in FIG. 12.
FIG. 14A shows a 4-panel die-cut item in the form as severed in FIG. 13.
FIG. 14B shows the 4-panel item following printing.
FIG. 15A shows the first step in the folding operation for this item.
FIG. 15B shows the second step in the folding operation.
FIG. 16 shows the completed dimensional piece in its open position.

As illustrated in FIG. 12, a web 75 of sheet material is unrolled and then re-rolled after fabricating; if desired, it could be run in the opposite direction so that it would be oriented for installation in the point-of-sale dispenser at the end of fabrication. The web 75 is designed to provide a series of structurally identical blanks 83 each of which will provide 4 panels in the ultimate greeting card piece or the like. The web 75 is first die-cut to create a stand-out structure 77 in panel 79*a* while the other 3 panels remain imperforate. Following the die-cutting step, a strip of transfer tape 81 is applied to the panel 79*b*, aligned with a subpanel of the die-cut stand-out 77. Transfer tape carries a strip of pressure-sensitive adhesive which adheres to the desired location in the panel 79*b* and transfers to that panel because a release coating on the tape liner layer allows it to be readily removed, thus "activating" the adhesive for purpose of joinder by exposing the upper adhesive surface. Alternatively, c-adhesive could be applied as previously described and shown in respect of FIGS. 9 and 10. Following the application of the transfer tape 81, the fabricated web 75 is re-rolled.

The web 75 in roll form is then supplied to a greeting card printing and dispensing machine which utilizes such a roll stock to provide blanks 83 for personalized printing. As can be seen in FIG. 13, the web 75 in roll form is severed by a reciprocating blade or the like to create a single 4-panel sheet material blank 83. As best seen in FIG. 14A, panel 79*a* of the blank 83 is die-cut to form the stand-out structure 77 including a main body 85*a*, a rectangular base subpanel 85*b* and a linkage arm 87. The piece 83 is then appropriately printed by the computer-driven laser printer so that an illustration then appears on what will be the front of the folded card, i.e. the panel 79c, and the selected greeting and verse are printed on the panel 79*a* in which the stand-out is die-cut. The blank 83 is then folded first about a horizontal line 86*a*, as shown in FIG. 15A, and then, as depicted in FIG. 15B, about a vertical line 86*b*. After the recipient signs the card and adds any personal greeting desired, the transfer tape 81 is removed, activating the underlying pressuresensitive adhesive for joinder. When the greeting card is then closed and placed in an envelope, the base subpanel 85*b* becomes affixed to the facing panel 79*b*. When the greeting card is eventually opened by the recipient, the stand-out structure prominently arises from the plane of the panel 79*a* while remaining parallel thereto in attention-attracting fashion as depicted in FIG. 16.

Figures 17, 18, 19:
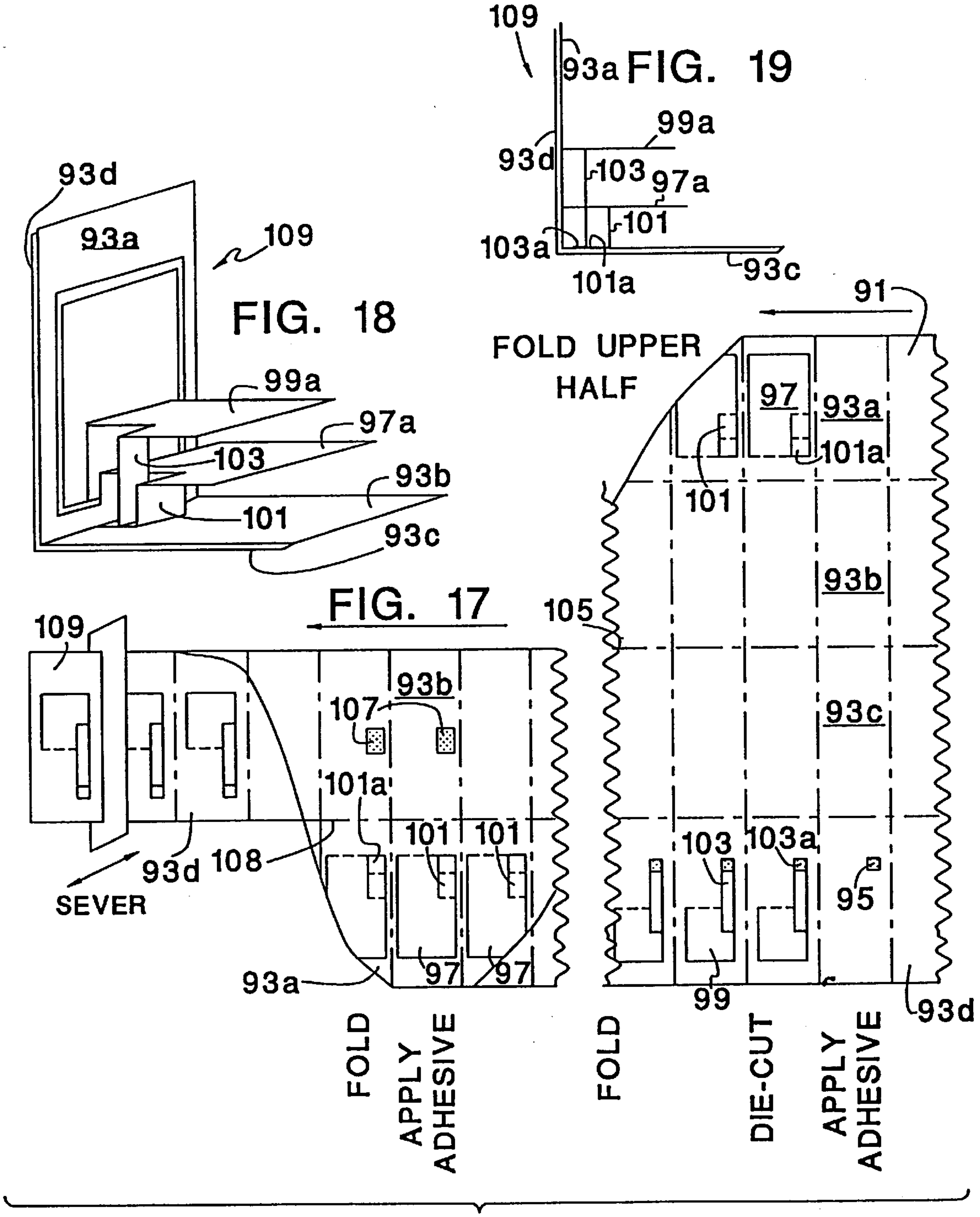
FIG. 17 shows a schematic view of a continuous web designed to be die-cut and treated to fabricate a series of structurally identical, 4-panel, dimensional items by folding the web twice as it moves from right to left.
FIG. 18 is a perspective view of a single dimensional item fabricated from the web of FIG. 17, which is shown in its open position.
FIG. 19 is a side view, reduced in size, of the 4-panel dimensional item of FIG. 18.

Illustrated in FIGS. 17–19 is a mass production method for transforming a continuous web of sheet material 91 into a series of structurally identical 4-panel, dimensional pieces. In this arrangement, the 4 panels of each blank extend completely across the web, which is moving from right to left, and the web is proportioned and printed so as to provide a plurality of blanks for fabricating structurally identical dimensional pieces. In the sequence shown, the web 91 for purposes of explanation should be considered to be divided into panels 93*a* through 93*d*. In the first step of the illustrated method, an adhesive pattern 95 is applied to the panel 93*d*. Next, both panels 93*a* and 93*d* are die-cut to provide stand-out structures 97 and 99. The stand-out structures respectively include a main body 97*a*, 99*a*, a linkage arm 101, 103 and a connecting subpanel 101*a*, 103*a*. As can be seen from FIG. 17, the subpanel 103*a* carries the adhesive pattern 95 that was earlier applied.

The upper half of the web 91 is then folded onto the lower half, causing the panels 93*a* and 93*d* to come into surface contact with each other. Folding occurs along a horizontal line 105, and so long as the central region of the web occupied by the panels 93*c* is substantially imperforate, it can be conveyed under high tension so that the fabrication operation can be run at high speed. As a result of this contact between the facing halves of the web, the connecting subpanel 103*a* becomes affixed to one surface, i.e. the undersurface, of the corresponding connecting subpanel 101*a* of the stand-out structure 97. After the folding is complete, a second adhesive pattern 107 is applied to the panel 93*b* aligned in a corresponding location to the upper surface of the subpanel 101*a*. Next, the web is folded a second time, i.e. along a line 108, so that the panels 93*a* become superimposed atop the panels 93*b*, in which position the adhesive pattern 107 affixes the other surface of the connecting subpanel 101*a* to the facing panel 93*b*. The web 91 is then severed by a reciprocating knife blade or the like to create a series of individual dimensional pieces 109.

When the piece 109 is opened, as depicted in FIGS. 18 and 19, the stand-out structures 97 and 99 move into a 3-dimensional orientation generally parallel to each other, and the linkages 101, 103 are proportioned so that the main bodies 97*a*, 99*a* are oriented generally perpendicular to the panel 93*a* when the opening angle is about 90°, as best seen in FIG. 19. The stand-out structures are moved to this orientation by the linkage arms 101 and 103 which are hinged at their upper ends to the main bodies 97*a* and 99*a* and are hinged at their lower ends to the connecting subpanels 101*a* and 103*a*. The subpanel 103*a* is affixed by the adhesive pattern 95 to the upper surface of the subpanel 101*a*, and the undersurface of the subpanel 101*a* is affixed by the adhesive pattern 107 to the imperforate panel 93*b*.

Figure 21:
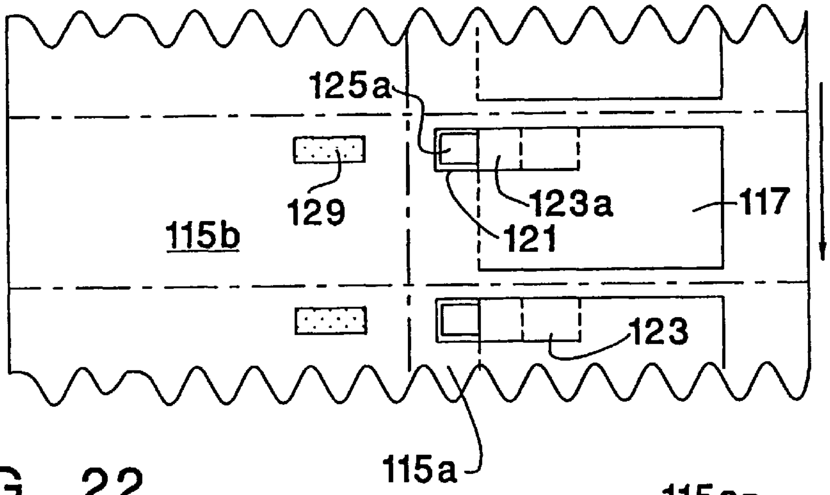
FIG. 21 is an enlarged view of a section of the web of FIG. 20.
Figure 22:
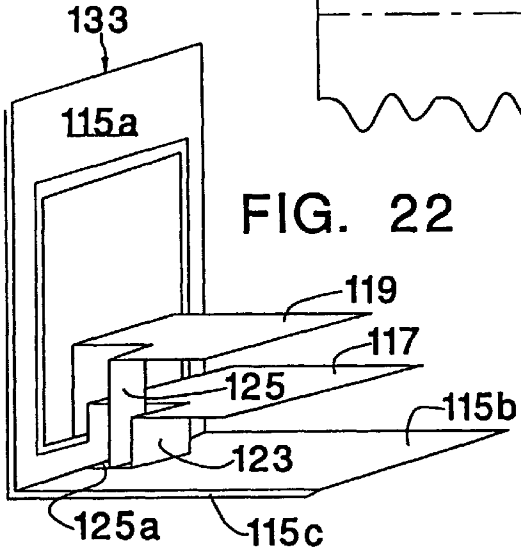
FIG. 22 is a perspective view showing the dimensional item fabricated from the web of FIGS. 20 and 21 shown in the open position.
Figure 20:
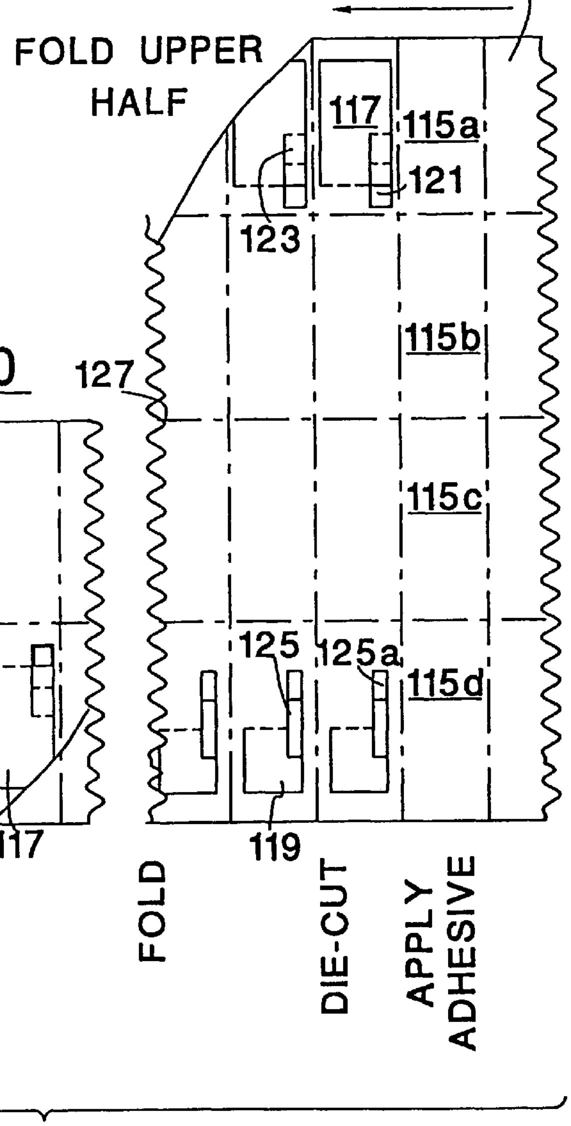
FIG. 20 is a view, similar to FIG. 17, showing an alternative embodiment of treating a generally similar web to produce a 4-panel dimensional item similar to that fabricated from the web shown in FIG. 17.
Figure 20:
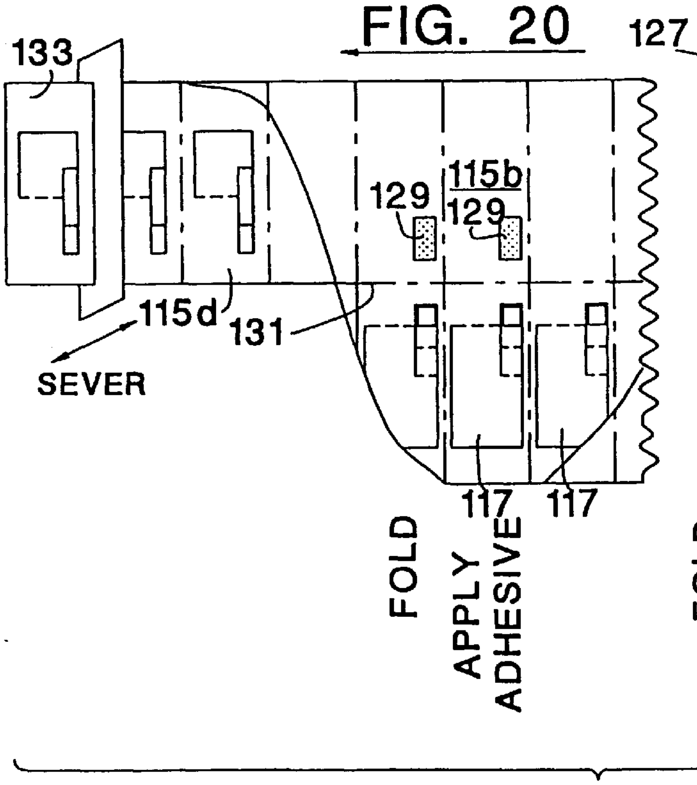

Illustrated in FIGS. 20, 21 and 22 is an alternative arrangement showing how dimensional pieces substantially the same as the pieces 109 can be created from a similar 4-panel across web arrangement using only a single adhesive-applying station. A similar web which is similar to the web 91, having 4 panels 115*a, b, c* and *d* is provided which is die-cut so as to produce a stand-out structure 117 in the panel 115*a* and a stand-out structure 119 in the panel 115*d*. However, in addition to the stand-out structure 117, an additional rectangular window 121 is die-cut adjacent the stand-out structure 117, and the small sheet material rectangle is removed by suction, or by air or mechanical means, from the web to leave the open window 121. The stand-out structure 117 has a linkage arm 123 with a connecting subpanel 123*a* that is generally the same as in the FIG. 17 configuration. The stand-out structure 119 has a linkage 125 which includes an elongated connecting subpanel 125*a* that, after folding, extends into alignment with the region of the open window, as can be seen in the left-hand portion of FIG. 20 and in the enlarged view shown in FIG. 21.

The web is folded along a horizontal centerline 127 so that the panels 115*a* and 115*b* are superimposed atop the panels 115*c* and 115*d*. An elongated adhesive pattern 129 is then applied to the panel 115*b* in a location where it will be aligned with both the subpanel 125*a* that is located just below the window and the subpanel 123*a* of the other linkage. The final folding step then takes place along a line 131 so as to place the panels 115*a* in surface-to-surface contact with the panels 115*b*, and subsequently, the twice-folded web is severed so as to create individual dimensional pieces 133.

When the piece 133 is opened, it appears essentially the same as the piece 109 illustrated in FIG. 18. Because of the presence of the window 121, both the connecting subpanel 125*a* and the connecting subpanel 123*a*are affixed to the surface of the panel 115*a* by the elongated adhesive pattern 129.

Figure 23:
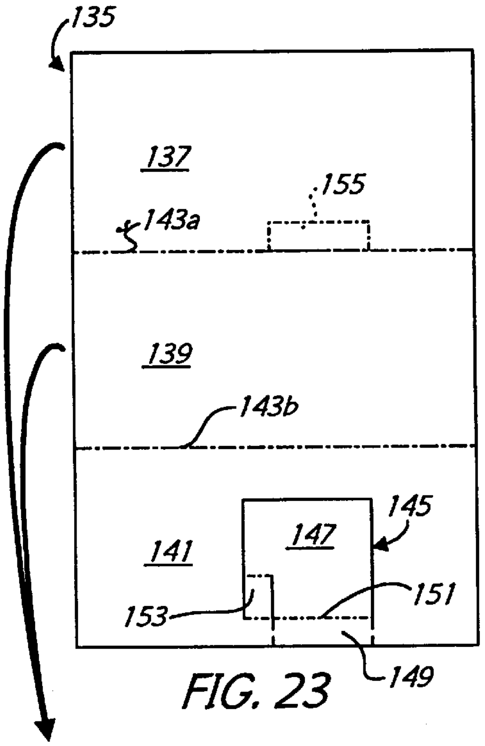
FIG. 23 is a plan view of a further blank embodying various features of the present invention having three panels which has been die-cut preliminary to forming another dimensional item.
Figure 24:
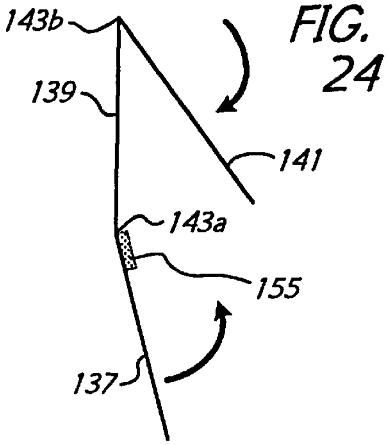
FIG. 24 is a side view of the blank of FIG. 23 showing steps in the fabrication of the dimensional item.
Figure 25:
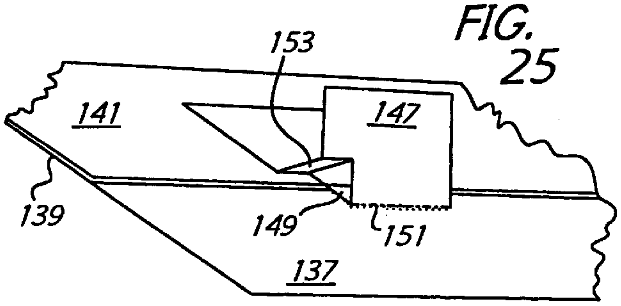
FIG. 25 is a fragmentary perspective view showing the fabricated dimensional item of FIG. 23 in its open configuration.

Illustrated in FIGS. 23, 24 and 25 is a blank 135 of sheet material for forming a 3-dimensional item. The sheet material may be printed either prior to or after die-cutting; for example, the blank 135 shown in FIG. 23 can be printed using a standard laser printer attached to a home computer or the like. The blank 135 contains three panels 137, 139 and 141 which are preferably of equal dimension and which are interconnected by lines of weakness or fold lines 143*a* and 143*b*. Die-cut in the lower panel 141 is a stand-out structure 145 which has a main body portion 147 and an underlying rectangular subpanel 149 which is hinged to the main body portion along a line of weakness 151 and which is disposed along the lower edge of the panel 141. A link 153 is hinged to the main body 147 and to the remainder of the panel 141 along parallel lines of weakness.

A rectangular adhesive region 155 is disposed on the undersurface of the panel 137, in alignment with the subpanel 149 of the stand-out structure. The nomenclature upper surface and undersurface are chosen simply to be descriptive with respect to the stand-out structure 145 and the surrounding portion of the panel 141 which will be prominent when the ultimate product is opened. The same surface of each of the panels 137 and 139 that will form the exterior of the folded item is also normally printed. However, it can be seen from FIG. 25 that it may also be desirable to also print the undersurface of panel 137. Adhesive region 155 can be any suitable adhesive, as for example remoistenable adhesive or pressure-sensitive adhesive covered with a release liner. Alternatively, it could be coadhesive with the corresponding surface of the subpanel 149 also being coated with coadhesive.

Manipulation of the blank 135 to form the fabricated item is shown in FIG. 24 where the panels 137 and 139 are folded so that the undersurface of panel 141 abuts the undersurface of center panel 139. At the same time or sequentially, the panel 137 is folded along the line of weakness 143*a* so as to lie atop the upper surface of panel 141, sandwiching it between the panels 137 and 139. The subpanel can be completely severed from the flanking portions of the panel 141 if desired; however, preferably the die-cutting is interrupted in these regions so as to leave a plurality of frangible bridges of paper fibers or the like which will interconnect the side edges of the subpanel 149 to the panel 141. Once adhesive attachment is established between the subpanel 149 and the panel 137 via the adhesive region 155, opening of the item from its folded condition will cause the rupture of these frangible bridges. Optionally, the undersurface of the panel 141 can be bonded adhesively or otherwise to the panel 139 so as to render the final structure shown in FIG. 25 more stable.

Figure 26:
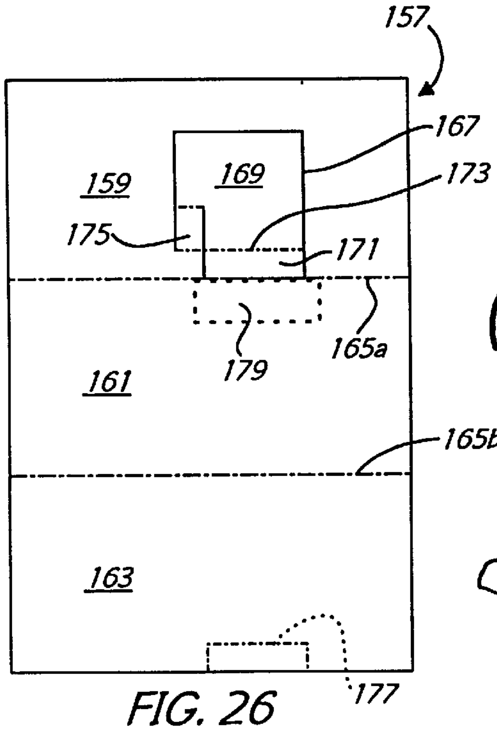
FIG. 26 is a plan view of still another blank embodying various features of the present invention similar to the blank of FIG. 23 for forming still another dimensional item.
Figure 27:
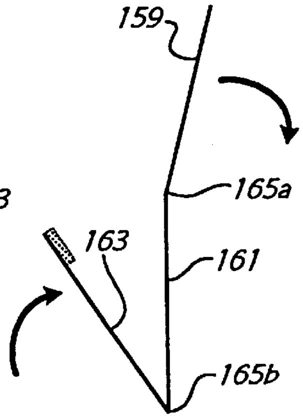
FIG. 27 is a side view of the blank of FIG. 26 showing steps in the fabrication of the dimensional item.
Figure 28:
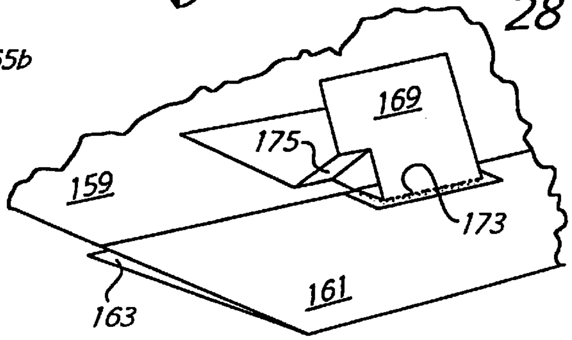
FIG. 28 is a fragmentary perspective view showing the fabricated dimensional item of FIG. 26 in its opened orientation.

Illustrated in FIGS. 26, 27 and 28 is an alternative embodiment of a blank 157 that is generally similar to the blank 135. The blank 157 is made of sheet material and is formed to have three panels of preferably equal dimensions, i.e., a top panel 159, a center panel 161 and a lower panel 163, which are respectively connected to one another along lines of weakness 165*a*, 165*b*. Die-cut in the upper panel 159 is a stand-out structure 167 which has a main body portion 169 and an underlying rectangular subpanel 171 that is hinged thereto along a line of weakness 173. A link 175 is hinged to the main body 169 and to the remainder of the panel 159 along a pair of parallel lines of weakness. Located on the undersurface of the lower panel 163, in general alignment with the subpanel 171, is an adhesive pattern 177 similar to the adhesive region 155 described above. Die-cut in the center panel 161, immediately adjacent the line of weakness 165*a*, is a rectangular plug 179 that is connected to the remainder of the panel 161 by perforations. Optionally, the rectangular plug can be simply removed at the time of die-cutting to leave a rectangular aperture at this location. However, if the perforated arrangement is used as illustrated, the plug 179 is removed either prior to or after the folding operation shown in FIG. 27. For example, the item can be delivered to a recipient in its unbonded orientation, with instructions to the recipient as to removal of the perforated plug and activation of the adhesive 177.

As shown in FIG. 27, the panel 163 is folded along the fold line 165*b* so that its undersurface comes in contact with the undersurface of the center panel 161, and the upper panel 159 is folded along the line of weakness 165*a* so as to sandwich the center panel 161 between the panels 159 and 163. When the perforated plug 179 is removed to leave an aperture having an area equal to at least a substantial portion of the area of the subpanel 171, that may be slightly larger than the subpanel 171 as illustrated, and the adhesive pattern 177 is activated, then upon folding the three panels into such surface-to-surface contact and optionally applying compression in the region of the subpanel 171, the subpanel 171 becomes bonded to the undersurface of the panel 163. As a result, when the item is unfolded by pivoting the panels 159 and 161 relative to each other, the stand-out structure 167, guided by the link 175, assumes the attention-attracting prominent position shown in FIG. 28, which illustrates the two panels completely opened so as to lie essentially in the same plane.

Another construction which utilizes an aperture in one panel to achieve bonding in the region of the subpanel that underlies the stand-out panel is shown in FIG. 1A as an alternative construction to that shown in FIG. 1. In the modified version of the blank, only one stand-out 17*a* is die-cut, and a square aperture 180 is die-cut in the central region of the subpanel 21*a*, and a hinged tab 181 is die-cut in the panel 13*b* along the fold line 15*a* and in alignment with the aperture 180. The hinged tab 181 is smaller in dimension than the subpanel 21*a* but larger than the aperture 180. An adhesive pattern 25' is applied to the panel 13*d* in the region adjacent and aligned with the aperture 180 or alternatively is applied to the undersurface of the tab 181. After folding is effected as shown in FIG. 2, the adhesive pattern 25' interconnects the hinged tab 181 to the upper surface of panel 13*d* (the surface seen in FIG. 3), thus sandwiching the subpanel 21*a* therebetween and effectively indirectly connecting the subpanel 21*a* in surface-to-surface contact with the panel 13*d*.

Illustrated in FIGS. 29 and 30 is a blank 182 of sheet material which contains three panels of preferably equal dimensions, a left-hand panel 183, a center panel 185 and a right-hand panel 187. The panels are separated by lines of weakness 189*a* and 189*b* about which they are folded in the fabrication process. Die-cut in the right-hand panel 187 is a stand-out structure 191 which is formed with a main body portion 193, a hinged subpanel 195 and a pair of flanking links 197 which are hinged to the body and to the remainder of the panel 187 along parallel lines of weakness.

The blank 181 is particularly suited for formation of fabrication of 3-dimensional items using a continuous web arrangement, such as generally described with regard to FIG. 17. For example, by first applying an adhesive pattern to the upper surface of subpanel 195 (or to the corresponding location on panel 185) and also to regions 199 on panel 183, and by folding panel 187 onto panel 185 and then panel 183 onto panel 187 as depicted in FIG. 30, an intermediate construction is achieved. Such adhesive application and folding can be efficiently carried out as part of a continuous web operation, if desired. Following the usual compression step, the web would be cut transversely to create a plurality of structurally identical items, and the right-hand edge, as viewed in FIG. 30, would be trimmed so as to provide a clean-cut edge and to separate the panel 187, which was die-cut to form the stand-out structure 191, from the panel 185 which serves as one of the outer cover panels of the final item. If desired, additional adhesive can be applied along the upper and lower edges of the panel 183, as illustrated by the regions 199*a* in FIG. 29, to produce a neater final product. Opening of the cover panels 183 and 185 causes them to pivot along the fold line 189*a* and the stand-out structure to assume a prominent, attractive 3-dimensional orientation generally similar to that shown in FIG. 25.

Illustrated in FIGS. 31–33 is a blank 201 made of sheet material which is formed with three panels of preferably equal dimension, i.e. a left-hand panel 203, a center panel 205 and a right-hand panel 207. The panels are interconnected by lines of weakness 209*a* and 209*b* about which folding occurs during the fabrication steps. As with the blank 181, the blank 201 is also well suited for fabrication as a part of a continuous operation on a web press. The blank 201 is also preferably formed with a horizontal line of weakness 211 which is used to form a false backbone as well known in this art and explained hereinafter. The right-hand panel is die-cut to form a stand-out structure 213 which includes a main body portion 215, a hinged subpanel 217, a link 219 which is hingedly connected to the main body and to the remainder of the panel 207 by a pair of parallel hinge lines.

As a part of a gluing and folding operation, an adhesive pattern can be applied to the upper surface of the subpanel 217 or to the appropriate location on the panel 205; adhesive is also applied in a backbone region 221 lying above the horizontal line of weakness 211 of either of the panels 205 or 207 as a step in creating the false backbone. Then, a first folding step is carried out to fold the blank along the line of weakness 209*b* to superimpose the die-cut panel 207 onto the center panel 205. Adhesive is also applied to the upper surface of the panel 203 in the false backbone region 221 and in the region that will generally flank the stand-out structure 213 upon the completion of folding; alternatively, such adhesive may be applied to the corresponding regions on panel 207. A second folding step is then carried out along the line of weakness 209*a* so that the panel 203 is superimposed atop the die-cut panel 207, and compression is preferably applied to assure that bonding is complete.

The continuous web is then cut transversely to create a plurality of structurally identical 3-dimensional items. Then, all four edges of the individual items are preferably trimmed to provide a neat appearance and to separate the panels 203 and 205, which serve as the cover panels of the fabricated item, in the region of the fold line 209*a*. Opening of the cover panels 203 and 205 causes pivoting along the horizontal line of weakness 211 and causes the main body portion 215 of the stand-out structure to rise in prominent 3-dimensional orientation guided by the link 219, as depicted in FIG. 33. Optionally, the stand-out structure 213 could be die-cut to have a rectangular configuration, and the two flanking rectangular portions of the panel 207 (see FIG. 33) could be stripped from the blank during the fabrication method.

Depicted in FIGS. 34–38 is a single panel blank 223 of sheet material that has been die-cut to form a stand-out structure 225 which includes a main body portion 227 and a pair of links 229. The main body 227 is hinged to a subpanel 231 which is generally T-shaped, having a leg section 233 and a crossbar section 235. The die-cutting is such so as to leave the remainder of the blank 223 in the form of a generally C-shaped frame 237 which surrounds the main body portion 227 of the stand-out and which is hinged at two spaced-apart locations at its left-hand edge to the crossbar section 235 of the subpanel along the lines of weakness 239.

The sheet material from which the blank 223 is formed has two surfaces which are referred to, for purposes of description, as an undersurface and an upper surface. The undersurface of subpanel 231 is shown in FIG. 34 and carries an adhesive pattern, which can be any suitable type of adhesive, such as pressure-sensitive adhesive, remoistenable adhesive, high-strength adhesive or the like. For example, if high-strength adhesive is employed, the blank can be substantially permanently affixed to a container or other carrier, whereas if pressure-sensitive adhesive is employed, the blank 231 may carry a releasable liner or may be attached to a surface of releasing character which permits its removal and disposition in a desired different location. For example, the blank 223 could be distributed in this manner as an attachment to a container for holding a sandwich in a fast-food restaurant chain. Sections of the undersurface of the three arms of the C-shaped frame could also be provided with a low-strength, dry-residue adhesive 243 that would further secure the blank in these regions to an underlying container or carrier on which it would be distributed, while still being easily releasable therefrom. The recipient could then remove the blank 223 from the container or carrier and affix it to a supporting surface of greater dimension, such as the supporting surface 241 depicted in FIG. 35, using the pressure-sensitive adhesive on the subpanel 231 to create a firm interconnection between the undersurface of the blank and the supporting surface 241.

The upper surface of the frame member 237 may optionally be provided with an adhesive pattern 245 which could be remoistenable adhesive or pressure-sensitive adhesive covered by a releasable liner. Once the blank 223 is secured in place on the supporting surface 241, the frame member 237 is grasped and pivoted upward and away from the stand-out structure 225, as depicted in FIG. 36, pivoting along the lines of weakness 239. As the frame 237 pivots still further, the links 229 pull the main body of portion 227 of the stand-out structure away from the supporting surface 241 as shown in FIG. 37. After the frame has pivoted 180°, the configuration shown in FIG. 38 is reached in which the main body portion 227 of the stand-out structure is prominently displayed. In this orientation, the frame is suitably interconnected with the supporting surface 241; for example, such interconnection can be by the optional adhesive pattern 245 or by interengagement with a tab 247 provided in the supporting surface by tucking it thereunder. In this orientation wherein the stand-out structure is prominently displayed, the frame 237 forms a background for it.

Alternatively, as illustrated in FIG. 38A, a blank could be provided wherein the middle arm of a C-shaped frame 237' is sufficiently wide to be doubled-over onto itself, and wherein a pattern of adhesive 249 is provided on the undersurface of the frame 237' generally along the right-hand vertical edge depicted in FIG. 34. Both the adhesive 249 and the adhesive coating the subpanel 231 may be pressure-sensitive adhesive; as such, the adhesive 249 would securely attach the blank 231 to a carrier having a releasing surface during distribution. Thereafter, following placement firmly on a supporting surface 241 and pivoting of the frame 180° as shown in FIG. 38, the folding over of the distal edge of the center arm of the frame allows the pressure-sensitive adhesive 249 to be used to interconnect the frame 237' to the supporting surface, carrying out the function of the tab 247 in FIG. 38. As another alternative, apertures in the end portions of the crossbar section 235 of the subpanel 231 could be created by removing kiss-cut perforated plugs to expose pressure-sensitive adhesive originally carried on the undersurface of the subpanel 231 which would then come in contact with the upper surface of the frame in regions spaced slightly from the fold lines 239.

FIG. 39 illustrates a blank 251 which is a single panel of sheet material that is die-cut to provide a main body portion 253 which is hinged to a central subpanel 255 along a line of weakness 257 and a pair of links 259, each of which is similarly hinged along lines of weakness 261 to the main body portion. The links 259 are also hinged along lines of weakness 263 to the remainder of the blank which in this instance constitutes a pair of link subpanels 265. The die-cutting is such that the link subpanels 265 are not totally severed from the central subpanel 255 which they flank. Instead, the die-cutting is interrupted in these two regions to create frangible bridges 267 which interconnect the three subpanels. As a result, the sheet material blanks 251 can be handled by high speed inserting equipment as though they were substantially uncut sheets because this essentially integral edge is not subject to flapping which would disrupt such high speed handling.

Shown in FIG. 40 is a schematic representation of how such blanks 251 might be utilized. Individual folders 269 of a size large enough to accommodate the blank 251 can be fed from a stack of such folders or otherwise provided as a part of a longitudinally moving conveying line. The folders could alternatively be provided as a part of a continuous web that is subsequently transversely severed to create individual folded items after the insertion of the blanks 251, or they could be provided in flat open condition. In any event, each folder 269 includes a front cover 271 and a rear cover 273. A folder is opened forward of the inserting station, and adhesive patterns 275 are applied at positions generally adjacent the fold line 277 between the covers and located so as to be in alignment with the link subpanels 265. At the insertion station, the blank 251 is positioned atop the rear cover 273, and the adhesive patterns 275 affix the link subpanels 265 to the interior surface of the rear cover. An adhesive pattern 279 is next applied to the upper surface of the central subpanel 255, or alternatively such is applied to the corresponding location on the interior surface on the front cover 271. The folder is then closed by pivoting the front cover about the fold line 277 to sandwich the blank 251 between the front and rear covers, and compression is preferably applied so as to assure that the adhesive pattern 279 strongly bonds the central subpanel 255 to the front cover 271. Thereafter, when the recipient receives the item and opens the covers 271, 273, the adherence of the central subpanel 255 to the front cover 271 and the flanking link subpanels 265 to the rear cover 273 causes the bridges 267 to rupture, and the links 259 accordingly cause the main body 253 of the structure to assume a prominent 3-dimensional configuration.

Illustrated in FIG. 41 is an alternative blank 281 where a stand-out structure 283 is die-cut in the blank leaving a surrounding frame 285. The stand-out structure includes a main body portion 287 and a hinged subpanel 289 together with a pair of flanking links 291 which are hinged along parallel lines of weakness to the main body portion 287 and to the frame portion 285. The lateral edges of the subpanel 289 are severed from the surrounding frame by interrupted die-cuts so as to leave frangible bridges 293 that continue to interconnect these adjacent sections of the blank. Preferably, the cutting die is also nicked at the locations marked midway along the three side edges of the main body 287 so as to provide greater integrity. The blank 281 can be inserted as shown in FIG. 40 by high speed insertion equipment. Preferably, instead of the two adhesive patterns 275, four patterns are provided on the interior surface of the rear cover of a folder, one located in alignment with each of the four corners of the blank 281. Opening of the front and rear covers 271, 273 causes the subpanel 289 to be pulled away from the frame 285 breaking the frangible bridges 293 and causing the main body portion 287 of the stand-out structure to assume a prominent 3-dimensional orientation.

Figure 42:
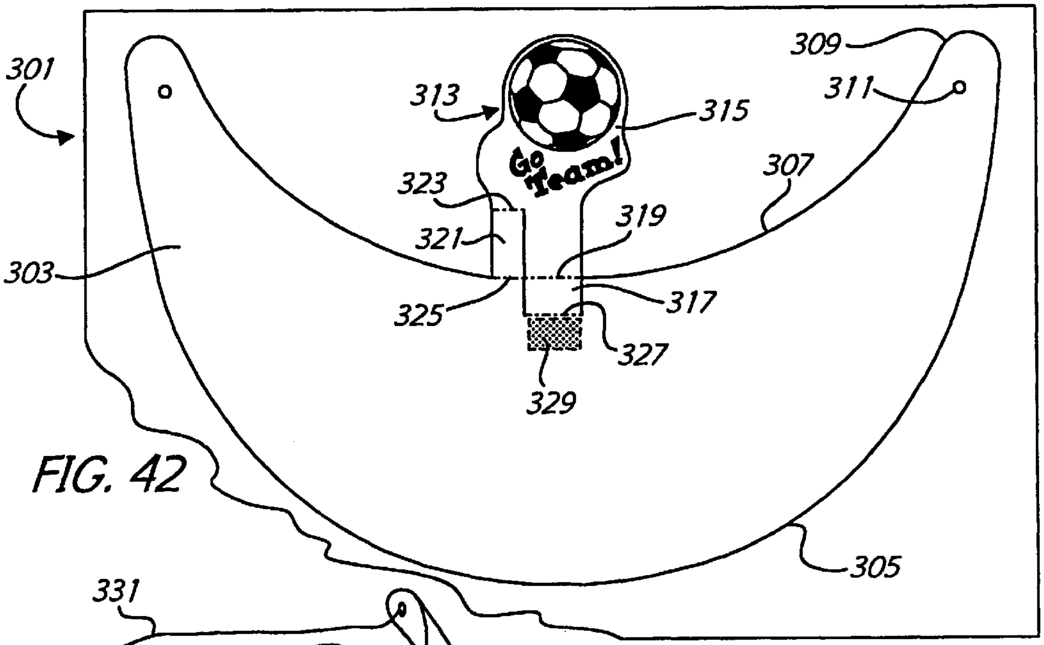
FIG. 42 is a plan view of a blank which has been die-cut to create a generally crescent-shaped sunvisor having hinged thereto a 3-dimensional structure.

Shown in FIG. 42 is a blank 301 for fabricating an attention-attracting sunvisor. The blank is preferably of rectangular shape and is made of sheet material in which there is die-cut a generally crescent-shaped sunvisor 303 which has a front or brim edge 305, a rear or crown edge 307 and a pair of opposite ends 309. Formed in each of the end portions is a small circular aperture 311 which provides means for attaching a band to secure the sunvisor to the head of the user; small slits may be alternatively used. Formed in the blank generally beyond the crown edge and located between the opposite ends 309 is a stand-out structure 313 which includes a main body portion 315 that is hinged to a subpanel 317 along a line of weakness 319 and hinged to a link 321 along a line of weakness 323. The link is hinged at its opposite end along a line of weakness 325 which intersects the rear edge 307 and which may be collinear with the line of weakness 319. The opposite end of the subpanel 317 is hinged to the body of the sunvisor 303 along a line 327 which is preferably parallel to the line of weakness 319. A pattern of adhesive 329 is located immediately adjacent and below the line of weakness 327 and is proportioned to be of about the same size and shape of the subpanel 317. The adhesive may be remoistenable adhesive or pressure-sensitive adhesive with a removable release liner disposed atop it, and such adhesive could alternatively be located on the subpanel 317 itself. A further option is to provide coadhesive both in the adhesive region 329 and on the subpanel 317.

The main body portion 315 is provided with an emblem of a product being advertised or with the insignia of a sports team or the like being supported. The die-cutting which creates the sunvisor 303 and the stand-out structure 313 can be created using a cutting blade that is repeatedly nicked, such as is commonly used to create microperforations, so as to allow the recipient of the blank to relatively easily separate the sunvisor and the stand-out structure from the remainder of the blank, or alternatively the entire outline could be formed using standard perforations. In either case, the blank 301 should have sufficient integrity to permit its customized printing in a standard sheet-fed printer.

Figure 43:
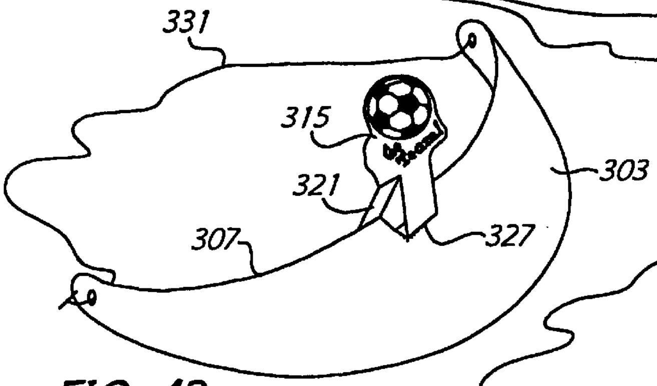
FIG. 43 is a perspective view showing the sunvisor following its removal from the blank of FIG. 42 and its manipulation so that the 3-dimensional structure is prominently disposed atop the sunvisor.

Once such separation of the sunvisor is effected, the subpanel 317 is bent along the lines of weakness 327 and 319 and pivoted 180° to bring it into surface-to-surface contact with the upper surface of the sunvisor 303 in the region of the adhesive pattern 329, which then interconnects the two surfaces. As a result of this movement, and guided by the hinged link 321, the main body portion 315 assumes a prominent 3-dimensional configuration above the sunvisor as shown in FIG. 43. Once an elastic band 331 or string or the like is attached to the sunvisor through the small circular apertures 311 or the like, the sunvisor is ready for use.

Figure 44:
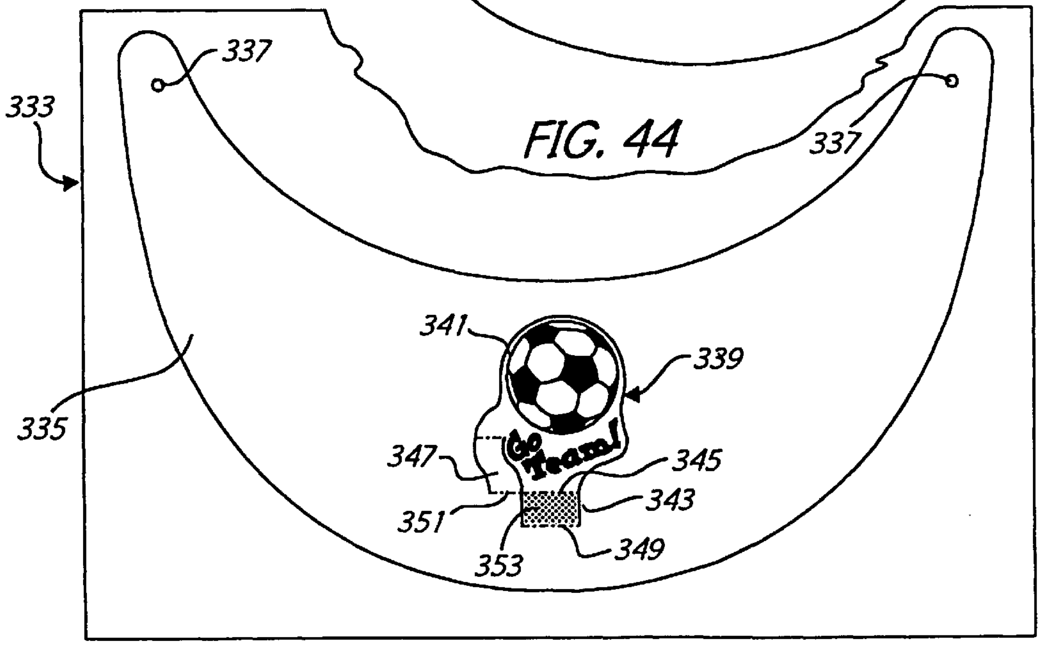
FIG. 44 is a plan view, similar to FIG. 42, showing another blank embodying various features of the invention in which has been die-cut an alternative embodiment of a crescent-shaped sunvisor.

Illustrated in FIG. 44 is an alternative form of a blank 333 wherein there is die-cut a generally crescent-shaped sunvisor 335 which is similarly formed with a pair of small apertures 337 near its opposite ends. In the sunvisor 335, a more centrally located stand-out structure is formed entirely within the region of the sunvisor itself so that it lies completely between the front and rear curved edges. The structure includes a main body portion 341 which is hingedly connected to a subpanel 343 via a line of weakness 345 and to a hinged link 347. The lower edges of both the subpanel 343 and the link 347 are connected along hinge lines 349, 351 respectively to the sunvisor itself. The upper surface of the subpanel 343 is covered with an adhesive pattern 353. As explained hereinbefore, the adhesive pattern may be alternatively located on the sunvisor body and may utilize an adhesive such as remoistenable adhesive or pressure-sensitive adhesive covered with a release liner, which could be transfer tape.

Figure 45:
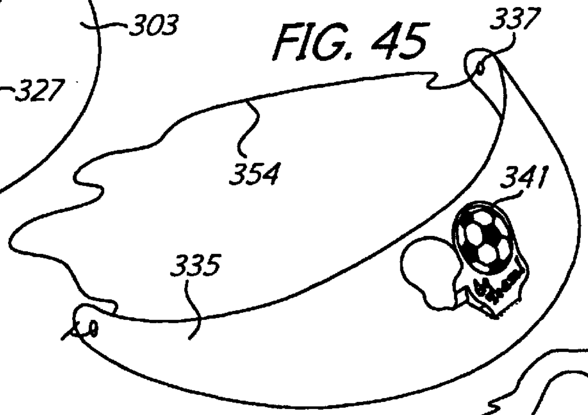
FIG. 45 is a perspective view, similar to FIG. 43, of the sunvisor formed from the blank of FIG. 44.

The outline of the sunvisor 335 and the stand-out structure 339 is preferably accomplished using a frequently nicked cutting die to create microperforations as previously mentioned so that the sunvisor remains a part of the blank and can be printed without difficulty in a sheet-fed printer or the like and distributed to the public; for example, the blanks may be handed out as a promotion at an athletic event on a sunny day. Once the sunvisor is removed from the blank, the stand-out structure is separated from the surrounding portion of the sunvisor so that creasing takes place along the lines of weakness which flank the link 347 and which flank the subpanel 343. After the adhesive is activated either by moistening remoistenable adhesive or removing the release liner from a pressure-sensitive adhesive pattern, or by applying via transfer tape, the subpanel 343 is pivoted 180° and thereafter becomes affixed to the upper surface of the sunvisor through the adhesive 353. An elastic band 354 or the like is then attached through the apertures 337 or the like, rendering the sunvisor ready for use. As shown in FIG. 45, the result of the interconnection of the subpanel 343 and the upper surface of the sunvisor is that the main body portion 341 of the stand-out structure guided by the link 347 assumes a prominent, attention-attracting configuration atop the broad brim of the sunvisor.

Figure 46:
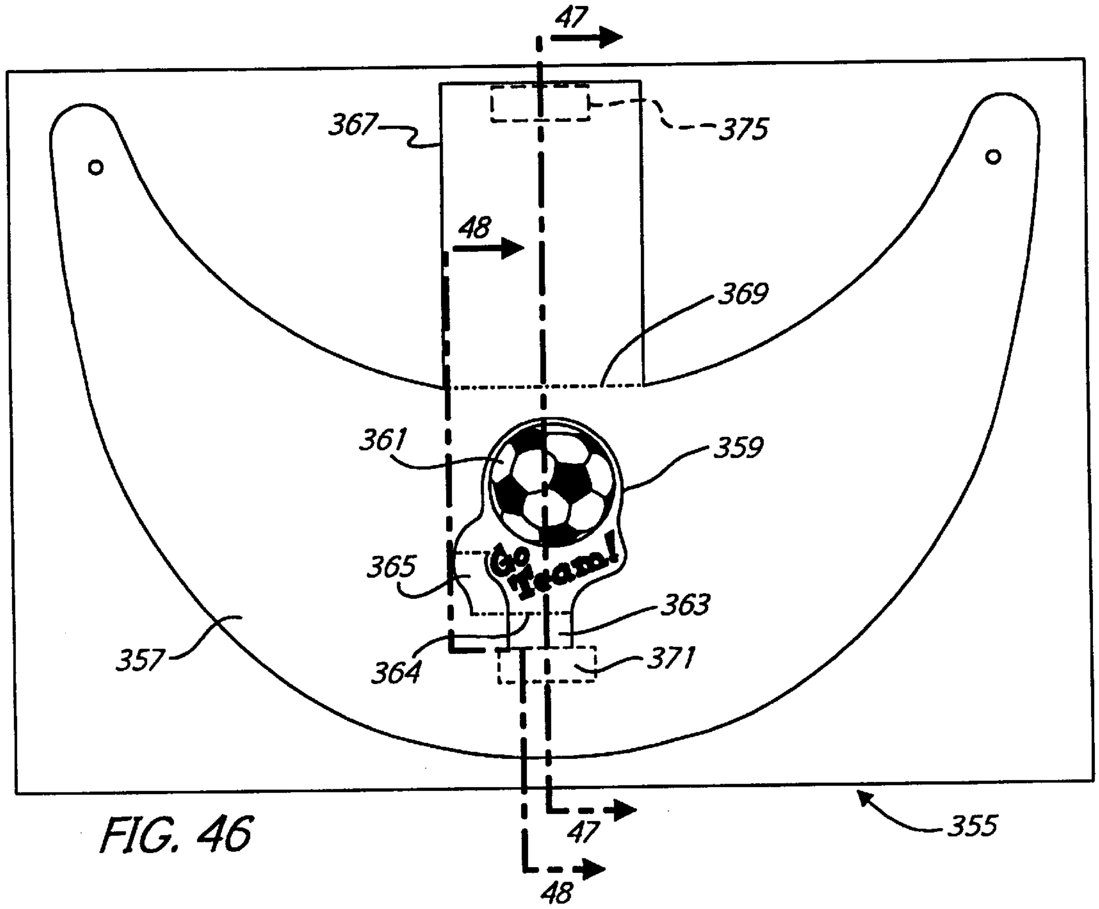
FIG. 46 is a plan view, similar to FIGS. 42 and 44, showing still another blank embodying various features of the present invention having die-cut therein a generally crescent-shaped sunvisor.

Illustrated in FIG. 46 is a blank 355 which is generally similar to the blank 333 in that it has die-cut therein a sunvisor 357 having a stand-out structure 359 die-cut therein which is located entirely between the front and rear curved edges of the crescent-shaped sunvisor. The stand-out structure 359 includes a main body portion 361 which is hinged along line 364 to a subpanel 363 located along its lower edge and also hinged to a link member 365. A rectangular filler panel 367 is die-cut in the blank so that it extends from the rear edge of the sunvisor, to which it is hinged along a line of weakness 369. Disposed in the sunvisor just forward of the subpanel 363 is a rectangular plug 371 that is connected by perforations to the remainder of the sunvisor. Removal of the plug 371 by punching it out of the plane results in an aperture 373. Located on the undersurface of the rectangular filler panel near the rear edge thereof is a rectangular adhesive pattern 375.

Figure 47:
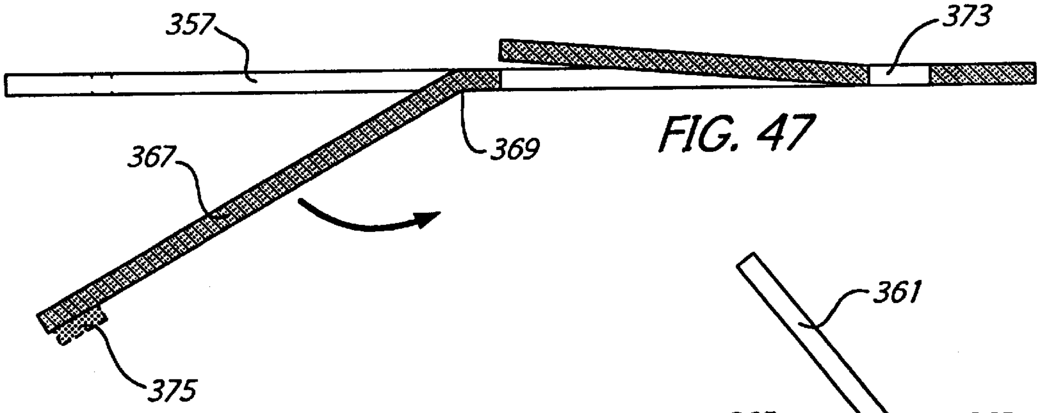
FIG. 47 is a sectional view taken generally along the line 47—47 of FIG. 46 which shows the sunvisor after it has been removed from the blank and as it is beginning to be manipulated to create the 3-dimensional structure.
Figure 48:
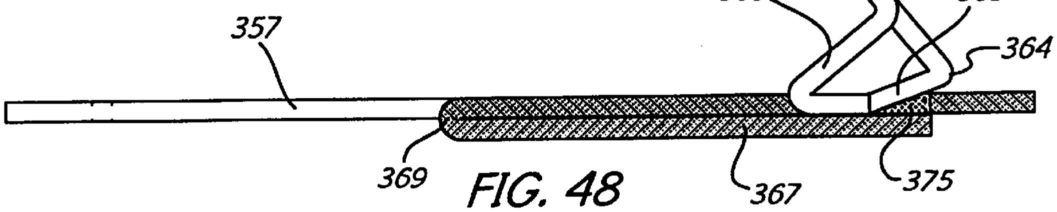
FIG. 48 is another sectional view similar to FIG. 47, taken along the line 48—48 of FIG. 46, showing the sunvisor after the manipulation has been completed to erect the attention-attracting 3-dimensional structure.

After the sunvisor 357 is separated from the remainder of the blank, the stand-out structure is pivoted out of the plane of the sunvisor guided by the link 365, the plug 371 is removed to create the aperture 373 and the subpanel 363 is bent along the line 364. The adhesive 375 is activated, for example by moistening remoistenable adhesive or removing a release liner from pressure-sensitive adhesive, and the rectangular filler panel 367 is pivoted along the line of weakness 369 as shown in FIG. 47. When the pivot panel is flush against the undersurface of the sunvisor as shown in FIG. 48, the adhesive 375 protrudes through the aperture 373, and the hinged subpanel 363 is pressed into contact therewith. This adhesive interconnects the subpanel and the filler panel 367, holding the stand-out structure in its prominent 3-dimensional configuration as shown in FIG. 48 set apart from the remainder of the sunvisor. The blank 355 is again one which can be printed by a sheet-fed printer or the like and then distributed to recipients. It is easily manipulated to form an attractive sunvisor which totally blocks the sun because the region from which the attractive, centrally located stand-out is removed is filled by the filler panel 367.

Although the invention has been described with regard to a number of presently preferred embodiments, which illustrate the best modes known to the inventors for carrying out the invention, it should be understood that various changes and modifications as would be obvious to those having ordinary skill in this art may be made without departing from the scope of the invention which is defined in the claims appended hereto. For example, the various types of adhesive and other bonding applications shown in any of these different embodiments are generally considered to be equally applicable to other of the illustrated embodiments and, as indicated before, other types of coadhesive and thermally or UV-activated adhesives can be employed. Generally, such adhesive can be applied to the opposite or facing panel from that illustrated, or to both panels. Also, the linkage lines of weakness preferably achieved during the die-cutting step might be omitted because of paper thinness or could inherently exist without being die-cut on a specific line when paper grain and strength design are so arranged. By substantially imperforate is meant that at least about 80% of the web is integral to provide structural strength adequate to run high speed fabricating, e.g. small apertures could be included in the panel in question without significantly detracting from strength. Although the invention has been illustrated, in part, with respect to fabrication from a continuous web, it should be understood that most of the illustrated embodiments are considered to be equally applicable to blanks that can be sheet-fed into suitable folding apparatus, or individually fed through copy machines or laser printers and then manually manipulated following printing, to achieve the desired finished pieces. The various lines of weakness, the linkages or the main body portions could be aligned angularly, as well as parallel, to a main hinge line, as shown in FIGS. 9–11. Although the disclosure often shows the folding of the interconnected panels of a web which is considered to have particular efficiency in mass-production operations, it should be understood that strips of a web each containing one of two such panels can be similarly hinged together along a straight line by severing the web and then manipulating the separate web portions to glue them together along a false backbone or the like, which is considered to be an equivalent of certain folding operations. Combinations of severing and folding steps may also be employed.

Particular features of the invention are emphasized in the claims that follow.

What is claimed is:

1. A blank designed for fabrication into a 3-dimensional item, said blank comprising a planar sheet of sheet material having an upper surface and an undersurface, die-cut means in said sheet forming a stand-out structure including a main body portion having at least one line of weakness therein which forms a hinged subpanel, said die-cut means also forming link means in said sheet, said link means being hinged to said main body portion of said stand-out structure and to the remainder of said sheet, and bonding means for interconnecting said subpanel of said stand-out structure to another region of said sheet so that interconnection between said subpanel and said sheet causes said stand-out structure to move prominently away from the remainder of said sheet, guided by said link means, and assume an attention-attracting orientation.

2. A blank according to claim 1 which is designed to be formed into a plurality of planar sections wherein said die-cut means is located along one edge of said planar sheet and in one said section of said planar sheet that is adapted to be superimposed upon another said section of said planar sheet and wherein said interconnection between said subpanel and said sheet that is accomplished through said bonding means connects the upper surface of said subpanel to a surface of another said section of said planar sheet.

3. A blank according to claim 2 wherein said link means includes a pair of first and second hinge lines which are parallel to each other and also to said edge of said planar sheet, said first hinge line being disposed between said edge of said planar sheet and said second hinge line and being located closer to said edge than to said second hinge line.

4. A blank according to claim 1 wherein said planar sheet has formed therein a second line of weakness which divides said planar sheet into at least first and second planar sections, with said die-cut means being located in said first section, wherein said bonding means is located on the undersurface of said second section, and wherein means defining an aperture is contained in one said section other than said second section and is located adjacent said hinged subpanel so that, after folding said second section beneath said other section along said second line of weakness, said bonding means is aligned with said aperture so as to permit said connection of said hinged subpanel to said second section through said aperture.

5. A blank according to claim 4 wherein said means defining said aperture comprises plug means connected by perforations to facilitate its removal.

6. A blank according to claim 1 wherein said planar sheet is designed to be formed into panels A, B and C, with said die-cut means being located in panel A, wherein panel A also includes a backbone subpanel connected to an edge of said hinged subpanel opposite to said at least one line of weakness, wherein said link means is connected by a hinge line to a link subpanel along an edge opposite from that at which it is hinged to said main body portion, wherein said blank is designed to be manipulated so that panel A is sandwiched between panels B and C, wherein said bonding means is located to interconnect said subpanel to panel B, and wherein additional bonding means is provided for interconnecting said link subpanel to panel C.

7. A blank according to claim 1 wherein said planar sheet is designed to be formed into panels A, B and C, with panel B being located between panels A and C and with said die-cut means being located in panel A, wherein said subpanel is located generally along one edge of panel A and said subpanel is connected to the remainder of panel A by frangible perforations, wherein said bonding means is located to interconnect said subpanel to panel B, and wherein additional bonding means is located to interconnect portions of panel A generally adjacent said frangible perforations to panel C.

8. A blank according to claim 1 wherein said hinged subpanel is generally T-shaped having a leg and a crossbar, said crossbar being hinged to said remainder of said sheet at the two spaced-apart locations, and wherein said remainder of said sheet includes a frame section which surrounds said main body portion.

9. A blank according to claim 8 wherein said bonding means comprises adhesive means located on said undersurface of said sheet which is positioned so as to bond portions of the undersurface of said subpanel to a supporting surface.

10. A blank for fabricating an attention-attracting sunvisor, said blank comprising a planar sheet of sheet material having first die-cut means therein creating a generally crescent-shaped sunvisor that has a pair of opposite ends, said ends being formed with means for attaching band means for securing said sunvisor to the head of a user, said sheet also having second die-cut means forming a stand-out structure in association with said sunvisor, which structure includes a main body portion having at least one line of weakness which forms a subpanel connected thereto, said second die-cut means also forming link means in said sheet which hingedly connects said main body portion of said stand-out structure to said sunvisor, and bonding means on said sheet for interconnecting said subpanel and said sunvisor so that such interconnection causes said stand-out structure to move prominently away from the remainder of said sunvisor guided by said link means to assume an attention-attracting orientation.

11. A blank according to claim 10 wherein said bonding means comprises adhesive means located either (a) on said subpanel of said stand-out structure or (b) on said crescent-shaped sunvisor of said planar sheet at a location generally adjacent said subpanel of said stand-out structure and in a position so as to interconnect said subpanel to said sunvisor.

12. A blank according to claim 10 wherein said stand-out structure is die-cut from said planar sheet in regions lying both inside and outside of said crescent-shaped sunvisor and wherein said link means is hinged to said sunvisor generally along a peripheral edge thereof.

13. A blank according to claim 10 wherein said stand-out structure is die-cut from said portion of said planar sheet material that forms said generally crescent-shaped sunvisor.

14. A blank according to claim 13 wherein said planar sheet has a planar upper surface and a planar undersurface, with said planar upper surface having printing at least in the region of said stand-out structure, wherein means defining an aperture is provided in said crescent-shaped sunvisor generally adjacent said subpanel of said stand-out structure, wherein a hinged filler panel of a size larger than said stand-out structure is die-cut in said planar sheet along a peripheral edge of said sunvisor, and wherein said bonding means is located on the undersurface of said filler panel at a location so as to be aligned with said aperture when said hinged filler panel is pivoted by folding along said peripheral edge so as to lie in surface-to-surface contact with the undersurface of said crescent-shaped sunvisor, whereby said bonding means forms said interconnection with said stand-out subpanel through said aperture and whereby said filler panel blocks openings in said sunvisor created when said stand-out structure is moved out of the plane of said sunvisor, which openings might otherwise permit passage of the sun's rays therethrough into the eyes of the wearer.

15. A blank according to claim 13 wherein said planar sheet has a planar upper surface and a planar undersurface, with said planar upper surface having printing upon at least the region of said stand-out structure, wherein a hinged filler panel of a size larger than said stand-out structure is die-cut in said planar sheet along a peripheral edge of said sunvisor, said hinged filler panel being located so that, upon folding to a location in juxtaposition with the undersurface of said crescent-shaped sunvisor, said filler panel blocks an opening in said sunvisor which is created when said stand-out structure is moved out of the plane of said sunvisor, and wherein means is provided for securing said filler panel in juxtaposition with the undersurface in said blocking position.

16. A blank according to claim 15 wherein said securing means constitutes adhesive.

17. A planar item for producing an attention-attracting sunvisor, said planar item comprising planar sheet material having the general shape of a crescent-shaped sunvisor that has a pair of opposite ends, said ends being formed with means for attaching band means for securing said sunvisor to the head of a user, said item also having a die-cut stand-out structure formed in association with said sunvisor, which structure includes a main body portion having at least one line of weakness which forms a subpanel connected thereto and link means which hingedly connects said main body portion of said stand-out structure to said sunvisor, and said sheet material having bonding means for interconnecting said subpanel and said sunvisor so that such interconnection causes said stand-out structure to move prominently away from the remainder of said sunvisor, guided by said link means, to assume an attention-attracting orientation.

18. A planar item according to claim 17 wherein said bonding means comprises adhesive means located either (a) on said subpanel of said stand-out structure or (b) on said crescent-shaped sunvisor at a location generally adjacent said subpanel of said stand-out structure and in a position so as to interconnect said subpanel to said sunvisor.

* * * * *